US012114996B2

(12) United States Patent
Kumpan-Bahrami

(10) Patent No.: US 12,114,996 B2
(45) Date of Patent: Oct. 15, 2024

(54) SYSTEM AND METHOD FOR IMPROVING A COSMETIC HAIR CONDITION

(71) Applicant: Henkel AG & Co. KGaA, Duesseldorf (DE)

(72) Inventor: Esther Kumpan-Bahrami, Duesseldorf (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 1273 days.

(21) Appl. No.: 16/629,460

(22) PCT Filed: Jul. 2, 2018

(86) PCT No.: PCT/EP2018/067838
§ 371 (c)(1),
(2) Date: Jan. 8, 2020

(87) PCT Pub. No.: WO2019/011704
PCT Pub. Date: Jan. 17, 2019

(65) Prior Publication Data
US 2020/0221994 A1 Jul. 16, 2020

(30) Foreign Application Priority Data
Jul. 10, 2017 (DE) .................. 10 2017 211 782.6

(51) Int. Cl.
A61H 7/00 (2006.01)
A61B 5/00 (2006.01)
(Continued)

(52) U.S. Cl.
CPC ............ *A61B 5/448* (2013.01); *A61B 5/0002* (2013.01); *A61B 5/0075* (2013.01);
(Continued)

(58) Field of Classification Search
None
See application file for complete search history.

(56) References Cited

U.S. PATENT DOCUMENTS 6,989,023 B2 * 1/2006 Black ................ A61H 23/0245
607/90
8,941,727 B2 * 1/2015 Rassman ............. A61B 5/1072
382/128

(Continued)

FOREIGN PATENT DOCUMENTS

WO 2004073537 A2 9/2004
WO 2009090632 A2 7/2009
(Continued)

OTHER PUBLICATIONS

EPO, International Search Report issued in International Application No. PCT/EP2018/067838, dated Oct. 10, 2018.

Primary Examiner — LaToya M Louis
(74) Attorney, Agent, or Firm — Lorenz & Kopf, LLP

(57) ABSTRACT

A system for improving a hair condition is provided in various embodiments. The system can have a sensor device having at least one sensor for detecting a hair condition parameter and a treatment device. The treatment device can have an illumination device for illuminating a scalp of a user with light and
an electronic circuit device coupled to the sensor device for receiving the detected hair condition parameter and/or a treatment parameter determined from the hair condition parameter by employing the sensor device, wherein the electronic circuit device can be configured to control an illumination of the scalp of the user using light by employing the illumination device based on the received detected hair condition parameter and/or the treatment parameter.

16 Claims, 12 Drawing Sheets

(51) Int. Cl.
*A61B 8/08* (2006.01)
*A61F 7/00* (2006.01)
*A61M 35/00* (2006.01)
*A61N 5/06* (2006.01)
*A45D 44/00* (2006.01)

(52) U.S. Cl.
CPC .......... *A61B 5/0077* (2013.01); *A61B 5/4836* (2013.01); *A61B 5/6803* (2013.01); *A61B 8/08* (2013.01); *A61F 7/00* (2013.01); *A61H 7/00* (2013.01); *A61H 7/006* (2013.01); *A61M 35/10* (2019.05); *A61N 5/0617* (2013.01); A45D 2044/007 (2013.01); A45D 2200/205 (2013.01); A61F 2007/0008 (2013.01); A61H 2201/0188 (2013.01); A61H 2201/02 (2013.01); A61H 2205/021 (2013.01); A61M 2205/3386 (2013.01)

(56) References Cited

U.S. PATENT DOCUMENTS

| | | | |
|---|---|---|---|
| 9,961,984 B2* | 5/2018 | Witchell | G01F 15/005 |
| 10,179,418 B2* | 1/2019 | Hendriks | A61B 18/203 |
| 2007/0179570 A1* | 8/2007 | De Taboada | A61H 7/006 |
| | | | 607/88 |
| 2008/0068604 A1* | 3/2008 | Grossinger | G01N 21/84 |
| | | | 356/328 |
| 2010/0139682 A1* | 6/2010 | Edgar | A61B 5/0071 |
| | | | 132/202 |
| 2010/0242155 A1 | 9/2010 | Carullo, Jr. | |
| 2011/0022132 A1* | 1/2011 | Kim | A61H 7/006 |
| | | | 607/91 |
| 2014/0100489 A1* | 4/2014 | Altshuler | A61H 99/00 |
| | | | 601/18 |
| 2015/0005854 A1 | 1/2015 | Said | |
| 2015/0032092 A1* | 1/2015 | Adanny | A61B 18/14 |
| | | | 606/9 |
| 2015/0366471 A1* | 12/2015 | LeBoeuf | A61B 5/742 |
| | | | 600/301 |
| 2016/0007908 A1* | 1/2016 | Guo | G01J 3/46 |
| | | | 348/77 |
| 2019/0216387 A1 | 7/2019 | Knuebel et al. | |
| 2019/0285546 A1 | 9/2019 | Knuebel et al. | |
| 2020/0221854 A1* | 7/2020 | Katzarov | G01N 21/3563 |

FOREIGN PATENT DOCUMENTS

| | | |
|---|---|---|
| WO | 2015190939 A1 | 12/2015 |
| WO | 2016125957 A1 | 8/2016 |
| WO | 2017198479 A1 | 11/2017 |
| WO | 2018007358 A1 | 1/2018 |
| WO | 2018166749 A1 | 9/2018 |

* cited by examiner

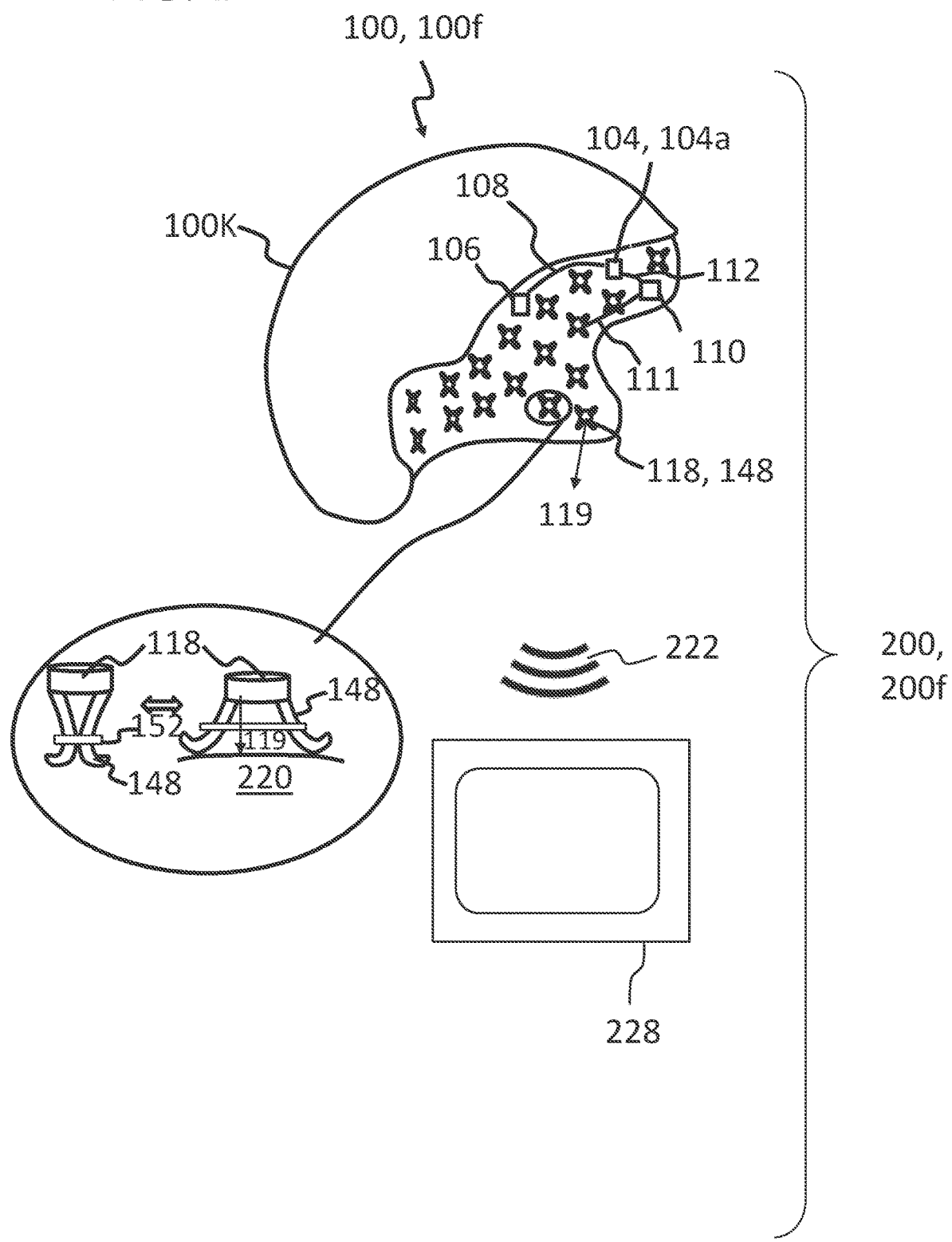

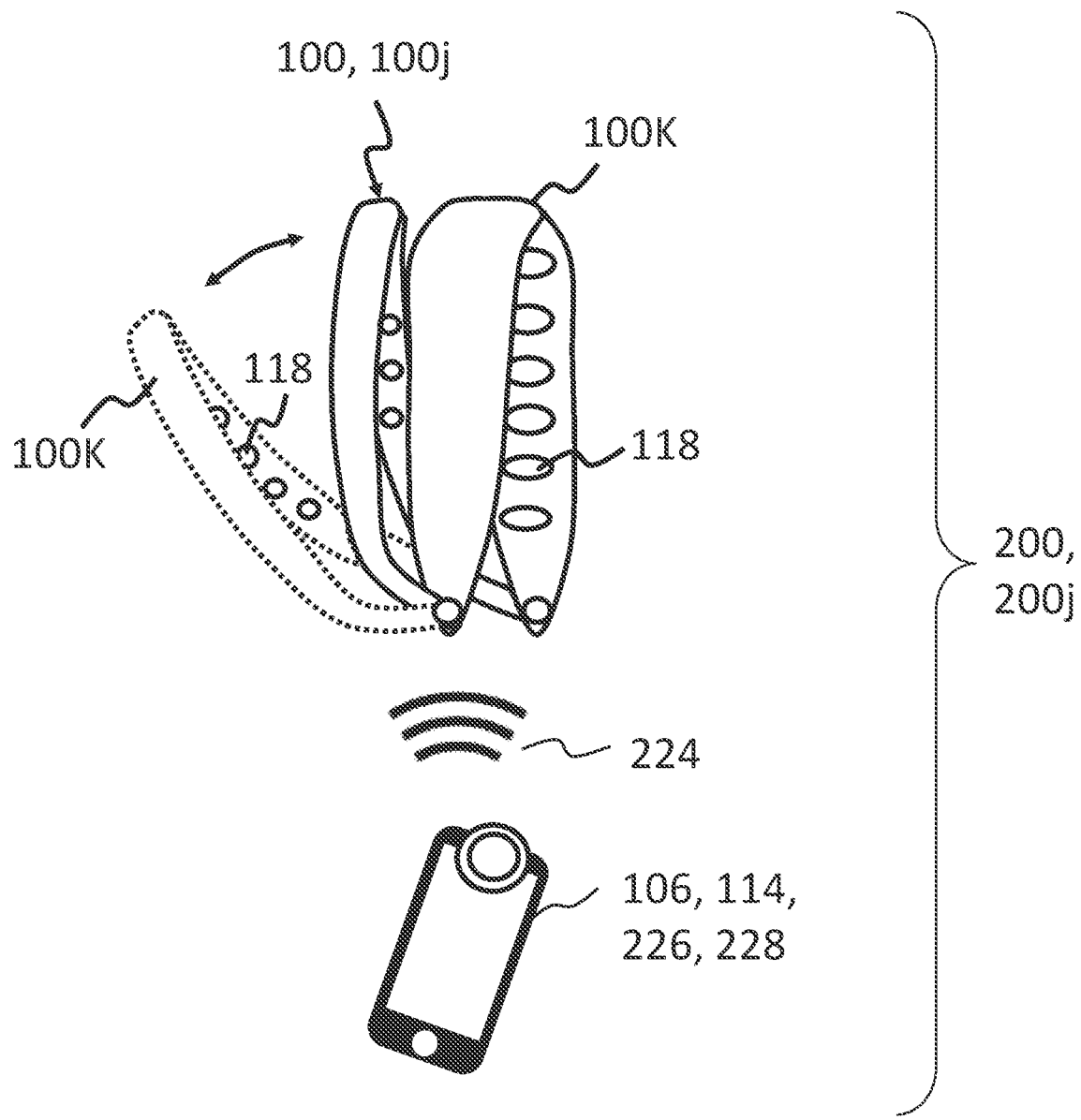

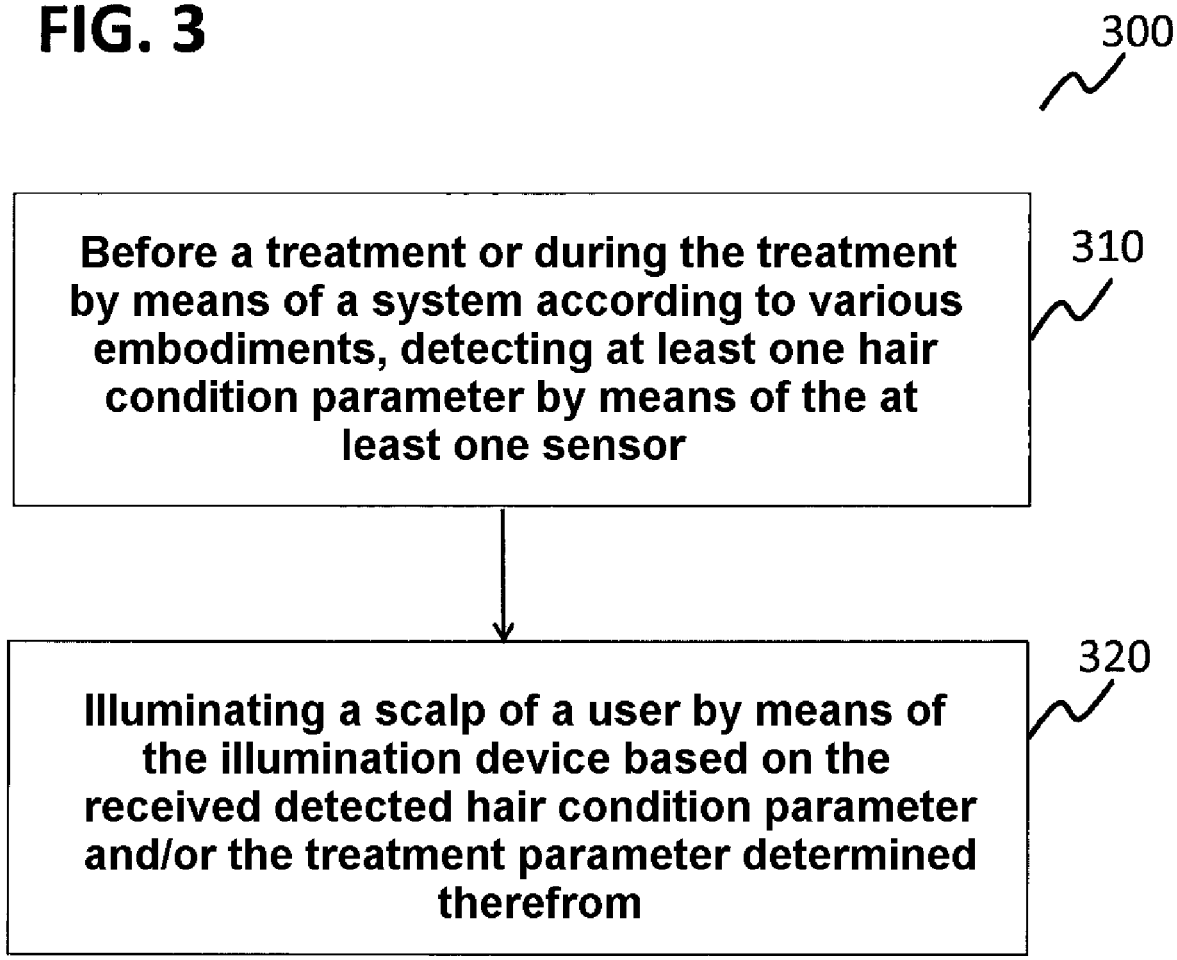

SYSTEM AND METHOD FOR IMPROVING A COSMETIC HAIR CONDITION

CROSS-REFERENCE TO RELATED APPLICATION

This application is a U.S. National-Stage entry under 35 U.S.C. § 371 based on International Application No. PCT/EP2018/067838, filed Jul. 2, 2018, which was published under PCT Article 21(2) and which claims priority to German Application No. 10 2017 211 782.6, filed Jul. 10, 2017, which are all hereby incorporated in their entirety by reference.

TECHNICAL FIELD

The disclosure relates to hair cosmetics, in particular a system for improving a hair condition and a method for the cosmetic treatment of hair.

BACKGROUND

In many areas of daily life, there has been a trend towards personalized programs that can respond to individual requirements and needs, for example, in a nutrition or health area, but also in an area of personalized cosmetics. This can enable a user to find targeted cosmetic products and/or to obtain care instructions that are matched to the individual needs of his hair, and thus enable a particularly high effectiveness.

For a user, it can be virtually impossible to reconstruct a treatment success, because the user, for example, at home, lacks opportunities to assess a treatment outcome in a standardized and objective manner.

Laypeople in particular can lack experience of how to deal with damaged hair and/or decreasing hair growth, for example, which care agents and/or hair growth agents and/or treatment methods are suitable.

In addition, it would be desirable to enable the user to objectively assess treatment success and/or course of treatment during a cosmetic hair treatment, for example, during a multi-part cosmetic hair treatment extending, for example, over an extended period of time.

BRIEF SUMMARY

This disclosure provides a system for improving a hair condition, having:
  a sensor device having at least one sensor for detecting a hair condition parameter; and
  a treatment device having:
  an illumination device for illuminating a scalp of a user with light; and
  an electronic circuit device which is coupled to the sensor device for receiving the detected hair condition parameter and/or a treatment parameter determined from the hair condition parameter by employing the sensor device,
  the electronic circuit device being configured to control an illumination of the scalp of the user with light by employing the illumination device based on the received detected hair condition parameter and/or the treatment parameter.

This disclosure also provides a method for improving a cosmetic hair condition of a user, having: before treatment or during treatment by employing the aforementioned system, detecting at least one hair condition parameter by employing the at least one sensor; and illuminating a scalp of the user by employing the illumination device based on the received detected hair condition parameter and/or the treatment parameter determined therefrom.

BRIEF DESCRIPTION OF THE DRAWINGS

The present disclosure will hereinafter be described in conjunction with the following drawing figures, wherein like numerals denote like elements, and:

FIGS. 1A to 1J each are a schematic illustration of a system for improving a hair condition according to various embodiments;

FIG. 3 is a flow chart of a method for improving a cosmetic hair condition according to various embodiments.

DETAILED DESCRIPTION

Figure 1A:
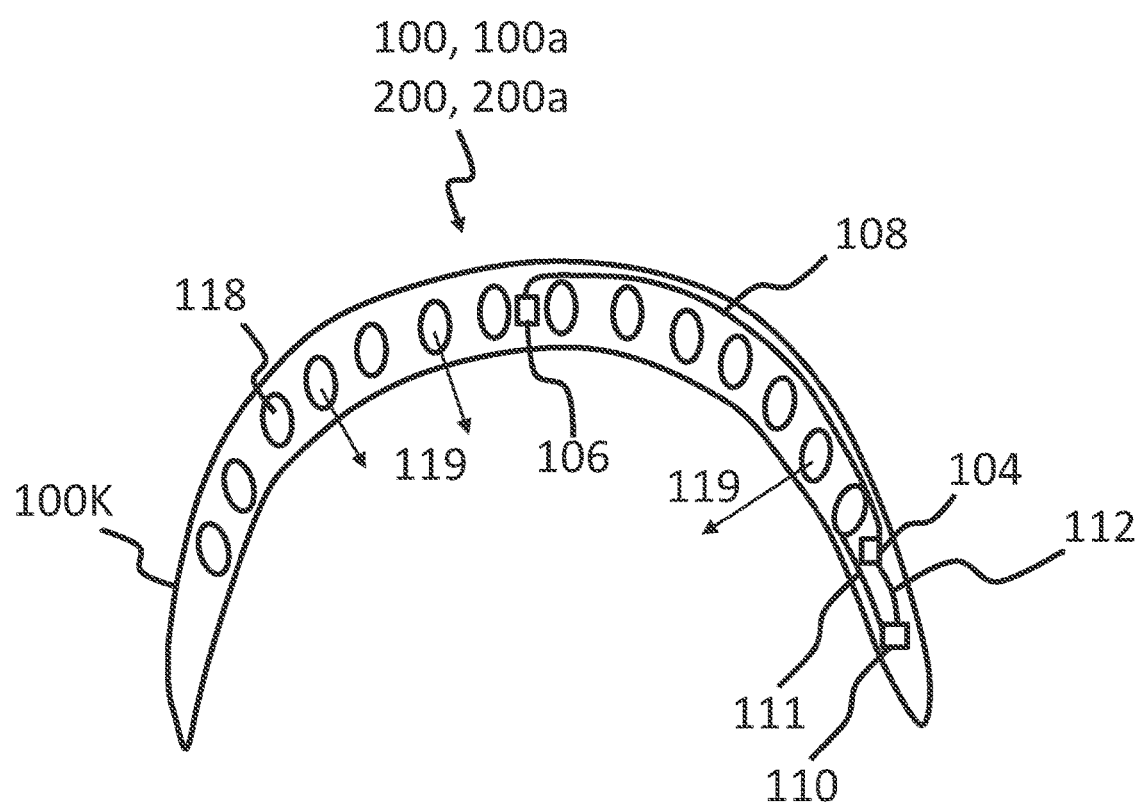

The following detailed description is merely exemplary in nature and is not intended to limit the disclosure or the application and uses of the subject matter as described herein. Furthermore, there is no intention to be bound by any theory presented in the preceding background or the following detailed description.

A system for improving a hair condition is provided in various embodiments. The system can have a small electric appliance, which can, for example, have a shape of a hair band, clip or helmet. The small electric appliance can also be a hand-held device.

In various embodiments, the system for improving a hair condition can have a sensor whose measurement result is taken into account when executing the hair treatment.

In various embodiments, a holistic ecosystem of intelligent/smart devices is provided, ranging from problem identification (analysis) to consultation (evaluation) to final provision of a desired benefit (smart small electric appliance, where appropriate, in combination with a suitable optionally individualized product), for example, providing an improved hair quality and/or a hair growth.

In various embodiments, a system for improving a hair condition can be provided, for example, a system for improving hair growth. The system for improving a hair condition can have, in various embodiments, a sensor device (also referred to as a sensor unit, analysis device, or analysis unit) and a treatment device (also referred to as a small electric device).

In various embodiments, the sensor device can determine a hair status, also referred to as a hair condition. The hair condition can have one or more hair condition parameters.

The sensor device can have a smartphone, a hair band, a comb or the like in various embodiments. The sensor device can be equipped with at least one sensor in various embodiments. In various embodiments, the sensor can a camera, for example, in conjunction with a microscope, a near-infrared sensor, a VIS/NIR sensor (that is, a sensor which is sensitive in a wavelength range which reaches from the range of visible light (VIS) to the near-infrared range (NIR), a sensor for detecting environmental conditions such as a humidity sensor, a temperature sensor, a wind sensor, etc.

In various embodiments, the treatment device can have an illumination device and be configured to illuminate a scalp of the user with light by employing the illumination device. In various embodiments, existing hair follicles in the scalp can be stimulated to increased hair production, for example, to form more and/or stronger hair.

In various embodiments, an effect promoting hair growth can be enhanced by employing combining the exposure with at least one other type of treatment of the hair and/or the scalp, for example, using a hair growth agent and/or using a massage of the scalp and/or using an application of temperature (heating and/or cooling the scalp).

In various embodiments, the treatment device can be configured to apply a hair treatment agent, for example, a hair cosmetic agent, to the hair and/or the scalp. The treatment device can be equipped, for example, with an integrated cartridge for this purpose. The hair treatment agent can be accommodated in the cartridge and dosed onto the hair by employing a dosing device, for example, by employing a spraying device and/or a dripping device.

The treatment device can be configured in various embodiments for applying a cosmetic agent and for applying mechanical work, for example, for massaging the scalp, for example, by employing an air flow and/or by employing rollers, and/or for applying temperature, for example, as an input of heat and/or cold into the scalp and/or hair, taking into account the data (and where appropriate, determined) detected by the sensor unit.

In various embodiments, the analysis unit and the small electrical appliance can be designed separately.

In various embodiments, the analysis unit and the small electrical appliance can be integrated.

In various embodiments, an intensity and/or a duration and/or a position of the treatment, for example, the illumination, the mechanical work and/or the temperature, can be controlled or regulated as a function of data transmitted/determined by the analysis device.

In various embodiments, the system for improving a hair condition can further have, for example, an input device, and/or an output device as an additional element.

In various embodiments, the input device can be a haptic and/or an acoustic input device.

In various embodiments, the output device can be an optical and/or an acoustic output device.

The input device can be used in various embodiments for inputting a control command (for example, starting, changing, stopping the system for improving a hair condition, and/or parts of the system for improving a hair condition, for example, only the treatment device or only the sensor device).

The output device can be used in various embodiments for outputting an analysis result and/or outputting a method and/or product recommendation and/or for outputting a treatment progress.

In various embodiments, the input and/or output device can be designed separately, that is, separately from the treatment device and from the analysis device.

In various embodiments, the input device can have a touch-sensitive screen, a keyboard, a microphone, a mouse, or the like, for example, as part of a smartphone, tablet, laptop, smart mirror, or the like.

In various embodiments, the output device can have a (for example, touch-sensitive) screen, a speaker, or the like, for example, as part of a smartphone, tablet, laptop, smart mirror, or the like.

In various embodiments, the input and/or output device can have a touch-sensitive screen, a combination of screen and keyboard, or a combination of microphone and/or speaker.

In various embodiments, the input and/or output device can be designed integrated into the sensor device, for example, as a touch-sensitive screen, as a combination of screen and keyboard, as a microphone and/or a speaker.

In various embodiments, the input and/or output device can be designed integrated into the treatment device, for example, the small electrical appliance, for example, as a touch-sensitive screen or as a combination of screen and keyboard, as a microphone and/or as a speaker.

The hair treatment agent which can be applied to the hair can, in various embodiments, be a commercial product, for example, a hair growth agent or a hair care agent.

In various embodiments, the hair treatment agent can be an individualized product, for example, an individualized product, which can be produced and provided or sent after a (for example, the first time) determination of the at least one hair condition parameter (that is, after an analysis of the hair, for example, by employing the sensor device).

In various embodiments, the individualized product can be produced after the determination of the hair condition parameter at home, at the point of sale of hair treatment agents or at the hairdresser, for example, by employing a mixing device for hair growth and/or care agents integrated into the system for improving a hair condition.

In various embodiments, the mixing device can be provided separately or, that is, is designed physically separate from the treatment device, the sensor device, and the input and/or output device.

In various embodiments, the mixing device can be integrated into the small electric appliance.

In various embodiments, the mixing device can be integrated into the separate input and/or output device.

In various embodiments, an improvement of the hair condition by an additive effect of hair growth and/or care agent and treatment device (that is, the mechanical (for example, massage) action and/or temperature effect by the treatment device) can be achieved or promoted. Alternatively, the improvement of the hair condition can be achieved or promoted by the synergistic action of the hair growth and/or care agent and treatment device (that is, the mechanical action and/or heat/cold action by the treatment device).

In a separate design of the sensor device, treatment device, input/output device and/or mixing device, communication can take place wirelessly within the multi-part system in various embodiments.

The wireless communication can be provided in various embodiments by employing a central communication hub.

In various embodiments, the communication can take place within a communication series formed from the individual components of the system in accordance with a sequence of processes.

In various embodiments, communication can occur within a network formed from the components of the system.

In various embodiments, a holistic system is provided which enables a standardized and objective assessment of a treatment outcome. In various embodiments, an optimization of a treatment result can be made possible with the aid of a broad set of data and experience (which is or can be made available to the system for improving a hair condition, for example, by the system for improving a hair condition accessing a processor cloud architecture (in short: cloud)).

In various embodiments, the system for improving a hair condition can be configured as a learning system. For example, other users' experiences can be continuously provided to the system for improving a hair condition, for example, by employing providing the experiences to the cloud by the other users, and, where appropriate, further processing the experiences in the cloud.

In various embodiments, a system is provided, which has a combination of a device for promoting hair growth (which is configured to promote hair growth by employing illuminating the scalp with light), a sensor, that is, at least one sensor (wherein the at least one sensor can be integrated into the device or physically separate from the device, for example, part of a separate sensor device), an electronic circuit device (for example, a processor, for example, a microprocessor) and an actuator (for controlling or regulating a hair treatment functionality of the device, for example, illumination control, temperature control or regulation and/or controlling or regulating a massage function).

In various embodiments, the combination can further have an input and/or output device and/or a mixing device.

Furthermore, in various embodiments, a method is provided which uses this system.

In various embodiments, the electronic circuit device can be configured to receive sensor data from the sensor, to evaluate the sensor data and, where appropriate, to compare the evaluated sensor data with at least one external database (for example, by employing a cloud).

In various embodiments, the processor can further be configured to derive handling instructions from the evaluated sensor data (for example, a process profile including illumination intensity and/or duration, where appropriate, position for the illumination, where appropriate, temperature and/or type and/or composition of the hair growth factors and/or care products used).

In various embodiments, the electronic circuit device can be further configured, where appropriate, to transmit handling instructions to the actuator, wherein the actuator can be part of the treatment device or the system for improving a hair condition.

In various embodiments, the actuator can implement the handling instruction provided by the electronic circuit device. An action performed by the actuator can, in various embodiments, turn the illumination device on/off and/or control or regulate an intensity of the illumination device, have a mechanical effect (for example, like controlling or regulating a massage function, and/or automatically adjusting a dosing device for a hair treatment agent at the treatment device), and/or the actuator can be configured to effect an automatic temperature adjustment.

In various embodiments, the at least one sensor can have a hair density sensor. The hair density sensor can have, for example, a camera or a camera attachment which can be configured to be held directly to a region of the hair root, for example, to be placed directly on a scalp. A hair density can be based on the image, for example, based on a number of hairs and/or a distance between the hairs, to determine the hair density. The sensor can provide the image of the scalp as an enlarged image, for example, using magnifying glass or microscope-like magnification, for example, magnification by a factor of about 2 to about 50, for example, a factor of about 10. In various embodiments, a smartphone camera having zoom function and/or having a microscope attachment can be used.

In various embodiments, the sensor can have a hair damage sensor. The hair damage sensor can be configured in various embodiments to determine, by employing near-infrared spectroscopy and/or fluorescence spectroscopy, an amino acid oxidation product content, in particular a cysteic acid content, of the hair and to determine a degree of hair damage therefrom. The hair damage sensor can be configured in various embodiments to determine a hair amino acid content of the hair by employing near-infrared spectroscopy and to determine a degree of hair damage to the hair therefrom. The hair damage sensor can be configured in various embodiments to record acoustic emissions detected during combing of the hair, and to determine the degree of hair damage of the hair therefrom, where appropriate, with the aid of the processor.

In various embodiments, the hair damage sensor can have a microscopic photosensor. The microscopic photosensor can be configured to detect a hair surface roughness or to enable the determination of hair surface roughness.

In various embodiments, the hair damage sensor can have a camera which can be coupled to an interference microscope of the sensor device.

In various embodiments, the sensor can have a hair thickness sensor. The hair thickness sensor can be configured in various embodiments to determine a hair thickness by employing a light sensor. For example, when determining the hair thickness, one can consider that thicker hair absorbs more light. In various embodiments, the hair thickness sensor can be configured such that a predetermined amount of hair, for example, single-layer, can be introduced into a given volume and the volume of light is irradiated with a predetermined intensity, wherein the amount of light that reaches the sensor after penetrating the hair can be measured by employing the sensor. The hair thickness can be determined on the basis of the detected light by employing the hair thickness sensor, where appropriate, in conjunction with the electronic circuit device.

In various embodiments, the hair thickness sensor, for example, in a case where the hair thickness sensor has a color camera, can also be used for determining a hair color, where appropriate, with the aid of the electronic circuit device.

The hair thickness sensor can have an ultrasound sensor in various embodiments. The ultrasonic sensor can be configured to emit ultrasonic waves in the direction of the hair, to detect ultrasonic waves reflected by the hair and, therefrom, where appropriate, in conjunction with the processor, to determine the hair thickness.

In various embodiments, the at least one sensor can have a hair length sensor. For example, the hair length sensor can have at least one position sensor which makes it possible to determine a distance covered in the hair. In various embodiments, the hair length sensor can be combined with a sensor for calculating combability of the hair (see below).

In various embodiments, the hair length can be provided by the user instead of determining the hair length by employing the hair length sensor. For example, the user can measure the hair length himself and provide the measured hair length value to the treatment device or the system for improving a hair condition.

In various embodiments, the hair thickness sensor can have a photo-optical sensor in which an image of at least one hair is recorded.

In various embodiments, the hair thickness sensor can have a thermal sensor.

In various embodiments, the sensor can have a straightness/curl sensor that can be configured to determine a hair structure in the sense of straight hair to curly or frizzy hair. The straightness/curl sensor can have a camera in various embodiments. The straightness/curl sensor can be configured in various embodiments, where appropriate, in conjunction with the electronic circuit device, for example, the processor, for example, by employing an image processing program, to determine a straightness or curl of the hair.

In various embodiments, the sensor can have a hair moisture sensor. The hair moisture sensor can be configured in various embodiments to determine a water content of the hair. The hair moisture sensor can, for example, be designed as a near-infrared spectroscope, which can be configured to examine near-infrared (NIR) absorption structures of water and, based on this, where appropriate, with the aid of the processor, to determine the hair moisture.

In various embodiments, the at least one sensor can have a combing work sensor. The combability sensor can be configured to detect a force (for example, by employing strain gauges), which is used in combing the hair.

In various embodiments, the sensor, for example, in the case of a spectrometer or a camera, can be configured to determine several hair condition parameters, for example, both the degree of hair damage based on the cysteic acid absorption structures in the NIR spectrum and the hair moisture based on the water absorption structures in the NIR spectrum.

In various embodiments, the sensor can be configured to determine further hair condition parameters.

In various embodiments, the treatment device of the system for improving a hair condition can have the illumination device and be configured to be controlled or regulated, depending on the result of hair analysis (in particular hair density, but also damage, hair thickness, curl, water content). For example, with lower hair density, the treatment device or the system for improving a hair condition can be controlled or regulated so that a higher effect to promote hair growth can be achieved than when detecting a higher hair density.

In various embodiments, the system can have, as a hair treatment unit, a device configured to perform mechanical work on the scalp, for example, to massage the scalp. For this purpose, the device can be equipped with nozzles for providing a massaging air flow and/or with a motor, for example, for driving massaging rollers. The massage function can be controlled or regulated by employing the (for example, electronically controllable) motor or the (for example, electronically controllable) nozzles.

In various embodiments, the treatment device can have an application device for applying the hair treatment agent to the hair or scalp. The application device can, for example, have a reservoir, also referred to as a tank or cartridge, and a dosing device, for example, at least one (for example, electronically controllable) valve and/or a (for example, electronically controllable) pumping device. The dosing device can be formed as part of the tank, and/or as part of a body of the treatment device, also referred to as a device body.

The cartridge can be refillable in various embodiments.

The hair treatment agent, for example, a hair growth agent and/or a care product can be located in the reservoir. Depending on the result of the hair analysis (for example, hair density, damage, hair thickness, curl, water content), the hair treatment agent, which can have, for example, a (for example, chemical) composition, can be applied to the hair by actuating the dosing device by employing the actuator.

In various embodiments, different volumes/amounts can be applied depending on the position (for example, occiput, receding hairline, other scalp area or onset, middle, tips of the hair) or applied to the scalp or hair.

In various embodiments, by employing the system for improving a hair condition, two or more agents in different mixing ratios can be applied to the hair or be capable of being applied, depending on position (for example, occiput, receding hairline, other scalp area or neck, center, tips of hair) or at different positions. For example, the hair growth agent can be applied to the scalp (where appropriate, in position-dependent dosage), and the hair care agent can be applied to the hair (where appropriate, in position-dependent dosage).

In various embodiments, a user can already receive information items about a course of the application while performing a hair treatment. A hair treatment result can still be optimized while performing the hair treatment so that frustration can be avoided.

In various embodiments, a system for improving a hair condition can be provided with a treatment device in which the at least one sensor is part of a separate communication-capable (that is, having a data exchange device) sensor device (for example, a smartphone having a camera (where appropriate, having a magnifying glass or microscope attachment), a spectrometer having the data exchange device, a so-called "acoustic comb", which can be configured to detect and transmit noise generated during combing, or the like).

An electronic circuit device that can have a processor and a first actuator that can have an illumination device can be integrated into the treatment device.

In various embodiments, the illumination device can emit light having a wavelength that promotes hair growth, for example, in a visible wavelength range, for example, between about 400 nm and about 500 nm, and/or between about 610 nm and about 690 nm, and/or in a near-infrared range, for example, in a range from about 800 nm to about 900 nm and/or from about 1000 nm to about 1200 nm, and/or in any other suitable wavelength range.

In various embodiments, the treatment device can have, as a further actuator, a temperature control or a temperature regulation which controls or regulates a temperature of at least one heatable or coolable surface of the treatment device, by employing which the hair and/or the scalp can be heated and/or cooled.

In various embodiments, the treatment device can have a data exchange device, for example, for receiving measured values detected by the at least one sensor and/or for receiving hair treatment parameters, for example, control statements.

In various embodiments, instead of being part of the separate communication-capable sensor device, the at least one sensor can be integrated into the treatment device or (for example, in the case of several sensors) in addition to it.

In various embodiments, the system for improving a hair condition, in addition to the electronic circuit device, can have a data processing device or can be configured to communicate with the data processing device. The data processing device can be communication-capable, that is, have a data exchange device, for example, part of a smartphone, a tablet, a laptop, a smart mirror or the like, on which, for example, an app can be installed, or, for example, a cloud or the like).

In various embodiments, the treatment device can have a data exchange device, for example, for receiving hair condition parameters determined by employing the sensor device or treatment parameters determined therefrom, and/or for receiving recommendations and/or control instructions determined by employing the data processing device.

By employing a software program, for example, a (smartphone) app, targeted information items, for example, control or regulation instructions, can be transmitted to the treatment device, which can be configured to control or regulate a hair treatment parameter based on the control or regulation instructions, for example, to dose a hair treatment agent, to set a temperature at which the hair can be treated, etc. A data exchange can be carried out here wirelessly, for example, via Bluetooth, WLAN, Thread or a Near Field Communication technology (NFC technology).

The illumination device can be controlled or regulated, for example, by employing a smartphone or the like, for example, by employing an app. The smartphone can form the data processing device which receives sensor data from the sensor device and/or itself provides at least one sensor, for example, the smartphone camera (where appropriate, in conjunction with a suitable app for determining at least one hair condition parameter, for example, a hair density, a hair color or the like). A treatment parameter can be determined by employing the smartphone based on the at least one received and/or determined hair condition parameter (for example, by employing a suitable software, for example, an app). For example, by employing the smartphone, an exposure time for each point of the scalp to be exposed can be determined, transmitted from the smartphone to the treatment device and illuminated by employing the treatment device using the illumination device.

In various embodiments, a system for improving a hair condition can be provided, which can have a treatment device, and can further have a data connection (the term connectivity is also used for the possibility of data exchange) between an external app and the treatment device. In various embodiments, hair treatment parameters can be provided, for example, predetermined, (for example, an illumination duration), wherein the parameter provided can be related to a hair density, that is, the hair treatment parameter can have a different value depending on the hair density.

In various embodiments, the input device can be configured to receive at least one input by the user and to provide it to the electronic circuit device and/or an external data processing device. Parameters or information items input by the user can have, for example, age and/or gender, a hair color or the like.

In various embodiments, one or more of the information items can be stored as part of a user profile, for example, in the electronic circuit device and/or in the external data processing device and thus retrievable again for later use.

The element controlled or regulated for controlling the hair treatment can further have, in various embodiments, an application or dosing device for the hair treatment agent and/or a heating and/or cooling device for heating the hair and/or a motor or a nozzle for massaging the scalp. The controlled or regulated element can, in various embodiments, be controlled by employing a wireless transmission device, for example, by the application device receiving control commands be employing the wireless transmission device. The wireless transmission device can be part of the electronic circuit device, for example. The wireless transmission device can, in various embodiments, have a chip or tag which enables wireless data transmission, for example, by employing Bluetooth, WLAN, Zigbee, NFC, Wibree, Thread, WiMAX or the like.

In various embodiments, prior to providing a recommendation to the user, a data comparison can be made between the smart treatment device and data, for example, reference data, which can be stored, for example, in a cloud. In various embodiments, the data can have data from other users having, for example, the same at least one hair condition parameter, and, for example, corresponding derived recommendations/measures.

In various embodiments, the determined recommendation can be used to produce an optimal/personalized hair growth agent or other hair care product and/or to initiate an online ordering of an optimal/personalized hair growth agent or other hair care product.

In various embodiments, a conventional hair treatment agent, for example, hair growth agent, can be used.

It is advantageous that an automatic reordering of the previously used hair growth agent or other hair care product takes place beyond a certain fill level. It can be preferred that, based on a change in the detected hair condition parameter, the user is advised to use another, more optimal hair growth agent or other hair care product.

In various embodiments, a user input can be used for the optimized delivery of hair treatment agent. The user can select the desired amount of product using a digital display and a touchscreen. For this purpose, a stored recommendation can already be programmed in the device, for example, stored in a database. A (quantity and) product recommendation can be made by employing a previous individual input, for example, a size of surfaces to be treated (for example, only the occiput on a surface having a given diameter, occiput and receding hairline corners, etc.). This can either be confirmed, extended or reduced by the user when, for example, he already knows that he tends to use more/less product than is normally stated on packaging.

In various embodiments, a method for the cosmetic treatment of hair is provided which allows a correct, that is, treatment and product selection suitable for a need for hair growth promotion or other hair care.

Herein, reference can be made to "the sensors", for example, regarding data transmission between the sensors and a data processing device, an arrangement of sensors, etc. It is to be understood that the sensors can have a totality of sensors arranged in the sensor device or the treatment device, for example, a totality of camera(s), temperature sensor(s), microphone(s), etc., or, if this is evident from the context, a part of said sensors.

In various embodiments, the system for improving a hair condition can have an electronic device, for example, a mobile electronic device (also referred to as a mobile device), for example, a smartphone or a tablet, or for example, another data processing device (for example, a PC). In various embodiments, the hair treatment system can also use an (where appropriate, further) external data processing device, for example, a cloud, for signal evaluation, for example, as an extension of the signal evaluation. For this purpose, in various embodiments, the signals detected by employing the sensors can be compared with signals stored in a database (also referred to as comparison signals, comparison data, reference signals or reference data). In various embodiments, the hair density, the degree of hair damage or another hair condition parameter can be classified based on this, for example, by assigning degrees of hair density values to the comparison signals, and assigning the hair density value or the other hair condition parameters of the comparison signal most similar to the measured signal to the measured hair.

In various embodiments, the reference data, which can, for example, be provided as a database, can be obtained empirically (for example, in the laboratory) for hair whose hair condition parameter (for example, hair density) can be known. In various embodiments, further information items about the hair can be present, which can serve as a basis for the reference data, for example, age, gender, hair color of the user, which in connection with an assessment of whether a determined hair density is normal or in need of improvement, and/or information items such as "hair bleached hair four times—high degree of damage" or "untreated hair—no damage", in the context of an assessment of degree of hair damage.

Furthermore, in various embodiments, the reference data can be detected, for example, several times in the course of a multi-part treatment. For example, how many treatments have already taken place can be parameterized as a degree of treatment.

In various embodiments, a user can be provided with an additional information item (for example, taken from the database), which degree of treatment corresponds to his hair condition, and/or how his hair condition is likely to develop when he performs a particular treatment, for example, performs a light treatment and/or applies a particular agent.

In various embodiments, for example, when using a cloud, the database can alternatively be generated (for example, continuously supplemented) in the laboratory by employing user data. In various embodiments, the database generated in the laboratory can be supplemented by employing user data which can be provided by employing the cloud.

In various embodiments, the recorded data, as described elsewhere herein, can be analyzed by employing software algorithms to determine a hair conditional parameter, for example, to determine a hair density (for example, number of hairs per unit area), degree of hair damage, or other parameters.

In various embodiments, for example, when the reference data are provided by employing the cloud, these can be available to a user at any time in order to be used as reference data for a comparison.

In various embodiments, the data detected by employing the hair treatment device or by employing the system for improving a hair condition can be stored, for example, in a memory integrated into the treatment device and/or into the external data processing device, for example, the cloud. The stored data can be stored so that at least the user is enabled to recognize this data as his data. This makes it possible to compare hair information obtained, for example, at different points in time (for example, before and after a treatment) with each other.

In various embodiments, the system for improving a hair condition can have a connection for transmitting (sending and/or receiving) data, for example, between a smartphone/tablet, which can be part of the system for improving a hair condition, and a cloud, and/or between the treatment device and the smartphone/tablet, and/or between the treatment device and the cloud, and/or between the sensor device and the treatment device and/or between the sensor device and the smartphone/tablet, and/or between the sensor device and the cloud.

In various embodiments, the analysis can be performed by the hair treatment device, for example, by employing the circuit device, and an analysis result can be transmitted to a display device, for example, to a display, a speaker, a smartphone, or the like, to provide the analysis result.

In various embodiments, the data can be transmitted to/on a data processing device, for example, on a smartphone with app, on a cloud, etc. After the data transmission to the data processing device, the examination of the data can be executed by employing this, for example, to determine a control and/or regulation parameter. In various embodiments, the data processing device can be part of the system for improving a hair condition, for example, in a case where the data processing device, for example, the smartphone or the like, is part of the sensor device and/or the input and/or output device or an independent part of the system for improving a hair condition (also referred to as integrated data processing device).

In various embodiments, the data processing device can be an external data processing device, for example, the cloud.

In various embodiments, the control or regulation parameter or recommendation can be determined directly by employing the system for improving a hair condition, for example, the treatment device and/or the sensor device and/or the input or output device and/or the other integrated data processing device, that is, the electronic circuit device and/or the integrated data processing device can be configured to determine the control/regulation parameter and, where appropriate, further information items itself (also referred to as directly). For example, the electronic circuit device can be or have a data processing device, for example, it can be equipped with a memory and a processor, for example, a microprocessor, which can be configured, for example, by employing programming, to receive the sensor data and to control or regulate the treatment device, and where appropriate, to provide information items to the user. For example, the sensor data can be compared to a database as described above.

In various embodiments, the electronic circuit device can be configured to indirectly determine the control or regulation parameter or the recommendation, for example, product or treatment recommendation. For example, the electronic circuit device (for example, in addition to a memory and a processor, for example, a microprocessor) can be equipped with a data transfer device which can be configured to transmit the sensor data received by the electronic circuit device to an external data processing device, for example, to a computer, for example, a cloud, by employing which, for example, as described above for determining the control or regulation parameter or the recommendation by employing the electronic circuit device, the control or regulation parameter or the recommendation can be determined in order to provide the control or regulation parameter or the recommendation, for example, by employing transmitting to the treatment device and/or to the display device and/or by employing transmitting the recommendation back to the electronic circuit device (for example, by employing the data transmission device). In various embodiments, the data transmission can take place in several stages, for example, by first transmitting the sensor data from the circuit device to the display device (for example, a smartphone, a tablet or the like), and the display device transmits the sensor data to the external data processing device (for example, the cloud).

A system for improving a hair condition is provided in various embodiments. The system can have a sensor device having at least one sensor for detecting a hair condition parameter and
a treatment device. The treatment device can have an illumination device for illuminating a scalp of a user with light and
an electronic circuit device coupled to the sensor device for receiving the detected hair condition parameter and/or a treatment parameter determined from the hair condition parameter by employing the sensor device, wherein the electronic circuit device can be configured to control an illumination of the scalp of the user using light by employing the illumination device based on the received detected hair condition parameter and/or the treatment parameter.

In various embodiments, the treatment device can have a hair band, a hair clip or a helmet.

In various embodiments, the at least one sensor can have at least one of a group of sensors, the group having: a camera for recording an image by employing visible light, UV light and/or near-infrared light for determining a hair density, a degree of hair damage, a curl, a hair color and/or a hair thickness, a microscope for determining a degree of hair damage and/or a hair thickness, a spectrometer for recording a spectrum of visible light, UV light and/or near-infrared light for determining a degree of hair damage and/or a hair moisture content, and an acoustic sensor for determining a degree of hair damage.

In various embodiments, the sensor device and the treatment device can be separate devices.

In various embodiments, at least a part of the sensor device and the data treatment device can form an integrated unit.

In various embodiments, the electronic circuit device can have a wireless data exchange device.

In various embodiments, the treatment device can have at least one further treatment element, wherein the treatment element can have an application device for a cosmetic treatment agent, a massage device, a heating device, and/or a cooling device, and wherein the electronic circuit device can be further configured, based on the received detected hair condition parameter and/or the treatment parameter, to apply the cosmetic treatment agent to perform a massage, to heat the scalp and/or hair and/or to cool the scalp and/or hair.

In various embodiments, the system can further have an input device and/or an output device.

In various embodiments, the input device can have a touch-sensitive screen and/or a keyboard and/or a mouse and/or a microphone, and/or the output device can have a screen and/or a speaker.

A method for improving a cosmetic hair condition of the user is provided In various embodiments. The method can have a detecting of at least one hair condition parameter by employing the at least one sensor before treatment or during treatment by employing a system according to various embodiments, and an illumination of a scalp of the user by employing the illumination device based on the received detected hair condition parameter and/or the treatment parameter determined therefrom.

In various embodiments, the method can further have a treating of the hair by employing the at least one further treatment element based on the received detected hair condition parameter and/or the treatment parameter determined therefrom.

In various embodiments, the treatment by employing the at least one further treatment element can have an applying of a cosmetic treatment agent to the hair or scalp, a massaging of the scalp, a heating the scalp and/or hair and/or a cooling of the scalp and/or the hair.

In various embodiments, the at least one treatment parameter can be determined from the at least one hair condition parameter in the electronic circuit device.

In various embodiments, the at least one treatment parameter can be determined from the at least one hair condition parameter in the electronic circuit device.

In various embodiments, the detection of the hair condition and illumination of the scalp can be executed repeatedly, wherein the detection of the hair condition at each repeated execution can be executed at a substantially similar location of the hair and/or the scalp.

In the following detailed description, reference is made to the accompanying drawings which form a part of the present application and in which is shown by way of illustration specific embodiments in which the disclosure can be practiced. In this regard, directional terminology such as "top", "bottom", "front", "back", "front", "rear", etc. is used with reference to the orientation of the described figure(s). Since components of embodiments can be positioned in a number of different orientations, the directional terminology is illustrative and is in no way limiting. It should be understood that other embodiments can be used and structural or logical changes can be made without departing from the scope of the present disclosure. It should be understood that the features of the various embodiments described herein can be combined with each other unless specifically stated otherwise. The following detailed description is therefore not to be taken in a limiting sense, and the scope of the present disclosure is defined by the appended claims.

Unless otherwise called "control or regulate", the terms "control", "controlled element", and so forth herein, unless otherwise described or otherwise understood by the context, are understood to mean "control or regulate", or "controlled or regulated element", etc.

FIG. 1A to 1J each show a schematic illustration of a system 200 for improving a hair condition according to various embodiments, wherein different embodiments are identified with trailing lowercase letters.

Figure 2A:
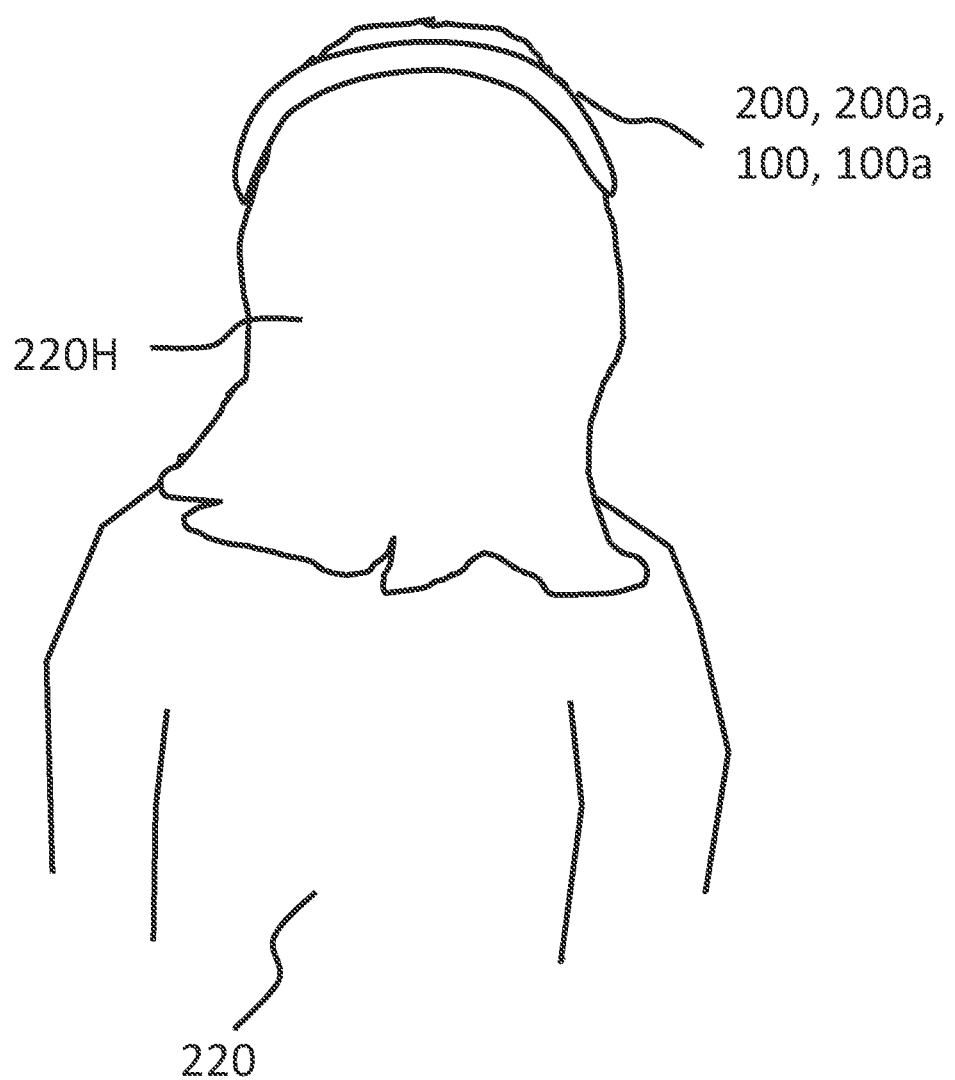
FIGS. 2A and 2B each are a schematic illustration of an application of a system for improving a hair condition according to various embodiments.
Figure 2B:
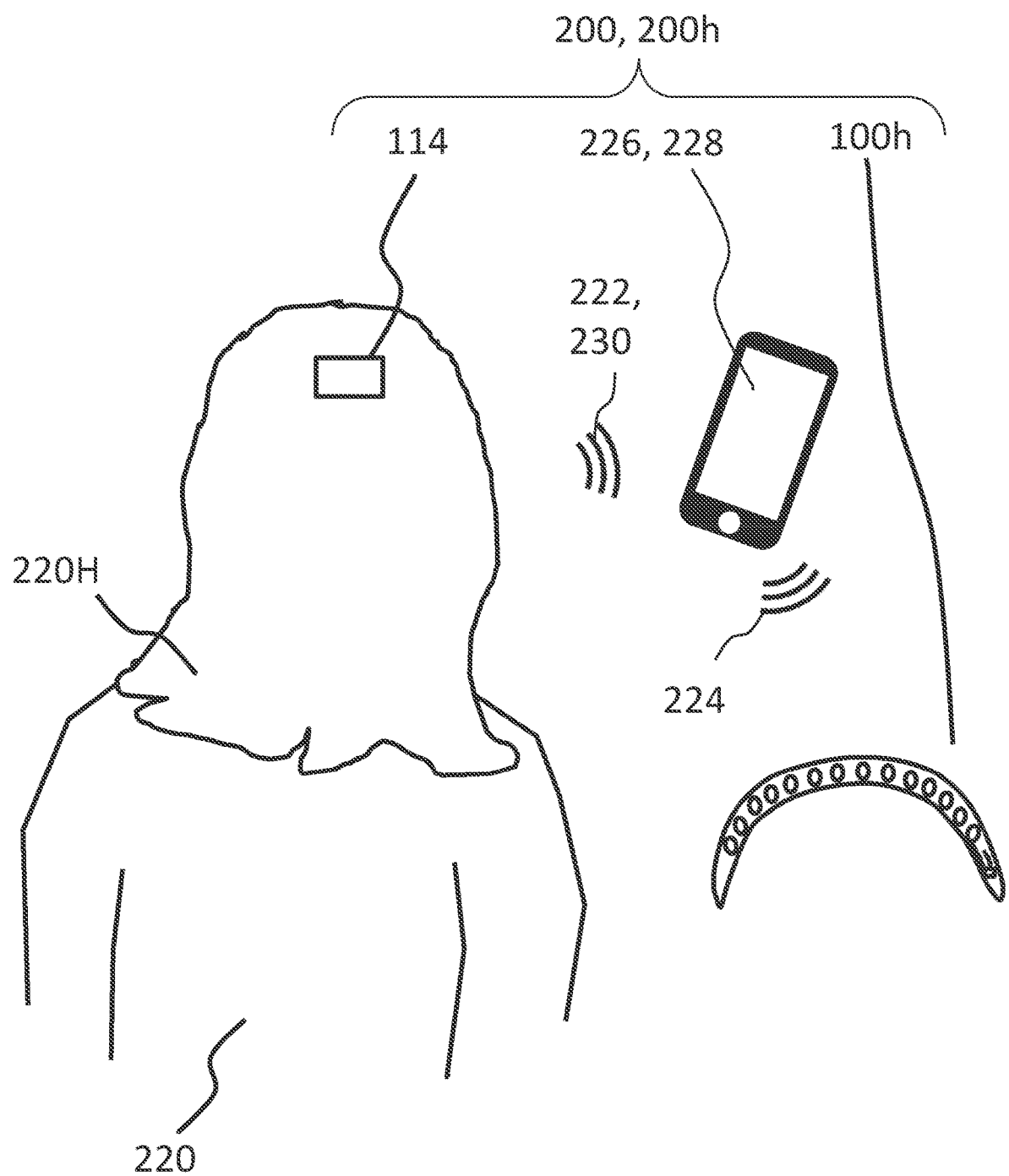

FIGS. 2A and 2B are each a schematic illustration of one application of a system 200 for improving a hair condition according to various embodiments.

In various embodiments, the system 200 for improving a hair condition has a treatment device 100 (various embodiments are labeled 100a, 100b, etc.).

In various embodiments, the treatment device 100 can have an electronic circuit device 104 arranged in or on the device body 100K.

The treatment device 100 can have a device body 100K. The device body 100K can be formed of or have such a solid material, for example, plastic or metal.

The device body 100K can be configured to be applicable to a head of a user 220 and/or movable along the head. Exemplary designs can be like a hair band, as, for example, in FIG. 1A, 1D, 1E, 1G, 1H, 2A, 2B or like a multi-part hair band as in FIG. 1J, comb-like as in FIG. 1B, block-like as in FIG. 1C or helmet-like in FIG. 1F, or having any other suitable shape that allows treatment to be performed by the device on the hair and/or scalp of the user 220.

In various embodiments, the treatment device 100 can further have a controllable or regulatable illumination device 118 that can be integrated with the device body 100K. The illumination device 118 can, for example, have a plurality of lights, for example, LED lights. The illumination device 118 can be configured such that, when using the treatment device, light 119 can be radiated onto the scalp of the user 220.

As described above, the light 119 can have a wavelength or wavelength range suitable for stimulating hair growth. In various embodiments, light 119 having these different wavelengths or ranges can be used in the treatment device 100 in combination. Preferably, the light 119 has a wavelength in the range of from about 640 to about 780 nm. Most preferably, the light 119 has a constant wavelength of about 655 nm (+/−5).

In various embodiments, a plurality of hair dividers 148 can be arranged on the hair treatment device 100, which plurality can be configured to divide relatively dense hair so that the light 119 can reach the scalp relatively unhindered. The hair dividers 148 can, as illustrated in FIG. 1B, be formed comb-like or brush-like, so that when combing/brushing (where appropriate, in both directions), the hair dividers 148 arrange the hair 220 in each case in intermediate spaces between the hair dividers 148 adjacent in a longitudinal direction of the brush, so that in each case adjacent light elements (for example, LEDs) are exposed in the transverse direction of the hair divider 148. The hair dividers 148 are not shown for clarity in some of the figures, but can be used in principle in each of the embodiments.

The hair dividers 148 in FIG. 1F can be designed in various embodiments so that even with a stationary arrangement of the treatment device 100f, as is achievable in a helmet, a region between the illumination device 118 (for example, LED elements) and the scalp of the user 220 of hair 220H is exposed so that the light 119 can reach the scalp unhindered.

FIG. 1F illustrates illumination device 118 and hair divider 148 enlarged in two configurations, left in a rest configuration and right while illuminating the scalp of user 220 with light 119, also referred to as an application configuration. A reset device 152 can be configured to guide the hair divider 148 (back) to the home position when the treatment device 200f is not in contact with the scalp of the user 220, and can be brought from the rest configuration to the application configuration when the treatment device 200f for treating the scalp (and where appropriate hair 220H) is arranged on the head of the user 220. For example, when brought to the application configuration, the hair dividers 148 can move radially away from the illumination device 118, thereby moving hair 220H away from the illumination device 118.

In various embodiments, the treatment device can have at least one further treatment element, wherein the treatment element has an application device 120 (see FIG. 1C) for a cosmetic treatment agent, a massage device, a heating device and/or a cooling device, for example, as described above. The electronic circuit device 104 can further be configured, based on the received detected hair condition parameter and/or treatment parameter, to apply the cosmetic treatment agent, to perform a massage, to heat the scalp and/or the hair, and/or to cool the scalp and/or the hair.

In various embodiments, the system 200 for improving a hair condition can have a sensor device 114 having at least one sensor 106 for detecting at least one hair condition parameter. The at least one sensor 106 can have one or more of the above-described sensors 106 and/or other/further sensors 106.

As stated above, the at least one hair condition parameter can have, for example, a hair density, a hair color, a hair moisture, a degree of hair damage, a hair thickness, a curl or the like.

In various embodiments, the at least one sensor 106 can be configured to detect more than one parameter, for example, the sensor 106 can have an NIR spectrometer that can be configured to detect both parameters for determining hair moisture and parameters for determining degree of hair damage, and/or the sensor 106 can have a camera, which (for example, by employing software) can be configured to determine parameters for determining the curl.

In various embodiments, as shown in FIGS. 1A, 1C, 1D, 1E, 1F and 2A, the sensor 106 can be arranged in the device body 100K, for example, be installed sealed. This can enable the treatment device 100 to be insensitive to moisture (in particular also to a moisture, where appropriate, of an applied hair treatment agent) and dirt.

Furthermore, the sealing can ensure that the treatment device can be cleaned without damaging the sensor 106 or another device. For example, the sensor 106 can be molded in by injection molding of the device body 100K.

In various embodiments, for example, when the at least one sensor 106 has or consists of an optical sensor, the device body 100K can be transparent between the sensor 106 and a surface of the device body 100K. In various embodiments, if it serves a purpose, the sensor 106 can be arranged in the device body 100 so as to face the hair 220H of the user 220 in a conventional arrangement of the hair on or in the hair treatment device 100 and/or can be in contact with the hair 220H.

In various embodiments, in which the sensor 106 is arranged in the device body 100K and the device body 100K can always be arranged in a substantially same position on the head of the user 220, such as the helmet of FIG. 1F or the head band, then detecting the sensor data by employing the integrated sensor 106 at substantially the same location of the head [[can]] be performed so as to enable reliable treatment course control.

In various embodiments, as shown in FIGS. 1B, 1G, 1H, 1J and 2B, the sensor 106 may not be integrated into the treatment device 100 but can be part of a separate sensor device 114. The separate sensor device 114 can, as illustrated in FIGS. 1B, 1G, 1H and 2B, in various embodiments, only be used to detect, where appropriate, process and transmit the detected and/or processed data.

In various embodiments, the sensor device 114 can also perform at least one additional function, that is, the sensor device 114 can, as shown in FIG. 1J, can be integrated with a further device of the system, for example, with an input and/or output device. In FIG. 1J, a smartphone can be used, for example, as a sensor, for example, by employing its camera, and its touch-enabled screen can be used as an input and output device. In addition, the electronic circuit device of the smartphone, which can have a processor and a memory, can be configured to perform an evaluation of the recorded data (for example, images) and, for example, determine a hair color, or the like, from an image showing hair 220H of the user 220. The determined hair condition parameter can be transmitted to the treatment device for controlling or regulating the treatment device.

The external sensor device 114 can have an electronic circuit device 1040 and a wireless data exchange device 1040a, which can be similar or identical to the electronic circuit device 104 and the wireless data exchange device 104a of the previous embodiments.

The electronic circuit device 104 can, in various embodiments, be coupled to the at least one sensor 106, for example, by employing a connection 108, for receiving the detected sensor value. In the presence of a plurality of sensors 106, the electronic circuit device 104 can have its own coupling to each of the sensors 106. The coupling can, in various embodiments, have or be an electrically conductive connection, a (glass) fiber connection and/or a wireless connection. The electronic circuit device 104 can be configured to receive the at least one sensor value from the at least one sensor 106.

In various embodiments, the electronic circuit device 104 can be or can have a data processing device, for example, can be equipped with a memory and a processor, for example, a microprocessor, which can be configured, for example, by employing programming, to receive the data from the sensor 106 and to derive one or more hair treatment parameters therefrom for controlling the treatment device, for example, as described above by employing controlling or regulating a temperature of the treatment device, a force exerted on the hair 102H of the user 102 (for example, in the form of a massage, for example, by employing an airflow and/or driven rollers), and/or a dosing of a hair treatment agent.

The thermal/mechanical elements of the treatment device can be controlled or regulated in each case by employing an actuator 110 in various embodiments.

For example, as mentioned above, the illumination device 118 can have an illumination control as an actuator, the heating device 122 can have a temperature control/regulation as an actuator 110, the exertion of the force on the hair can take place by employing a controllable/regulatable motor as an actuator 110, and/or the application device (nozzles 120 of the application device are shown in FIG. 1B) for the hair treatment agent can have a pump and/or a dosing valve as an actuator 110.

The actuator 110 can thus be configured to influence a hair treatment parameter. The actuator 110 can in each case be controlled or regulated such that the hair treatment parameter influenced by employing the actuator 110 corresponds to the hair treatment parameter determined on the basis of the hair condition parameter.

The electronic circuit device 104 can be configured in various embodiments to determine and provide to the user 220 at least one recommendation based on the received data from the sensor 106, for example, as described above, as a guidance video, as a product recommendation for a known hair treatment agent, or as a prescription for a user individual hair treatment agent as described above.

In various embodiments, for example, in a case where the at least one sensor 106 is used to determine a hair density, a degree of hair damage, a curl, or the like, the treatment device 100 can be configured to control the actuator 110, for example, one of the hair density, the degree of hair damage, the curl, or the like to realize appropriate illumination treatment, for example, by employing adjusting the illumination duration and position.

In various embodiments, the user 220 can also be provided with a hair treatment recommendation, for example, a recommendation "illuminate every part of the scalp to be treated for at least five seconds" or something similar.

In various embodiments, as shown in FIG. 1B, the actuator 110, for example, as an alternative or in addition to the temperature control or regulation, can have a controllable or regulatable application device 120 (also referred to as a dosing device) which can be configured to dose a hair treatment agent based on the detected sensor data.

As stated above, the application device 120 can have at least one pump and/or at least one valve, which can be controllable or regulatable such that a volume or a quantity of the hair treatment agent can be dosed. The dosing can be done in various embodiments depending on a position of the treatment device 100 on the hair 220H or on the scalp, for example, as described above.

Figure 1B:
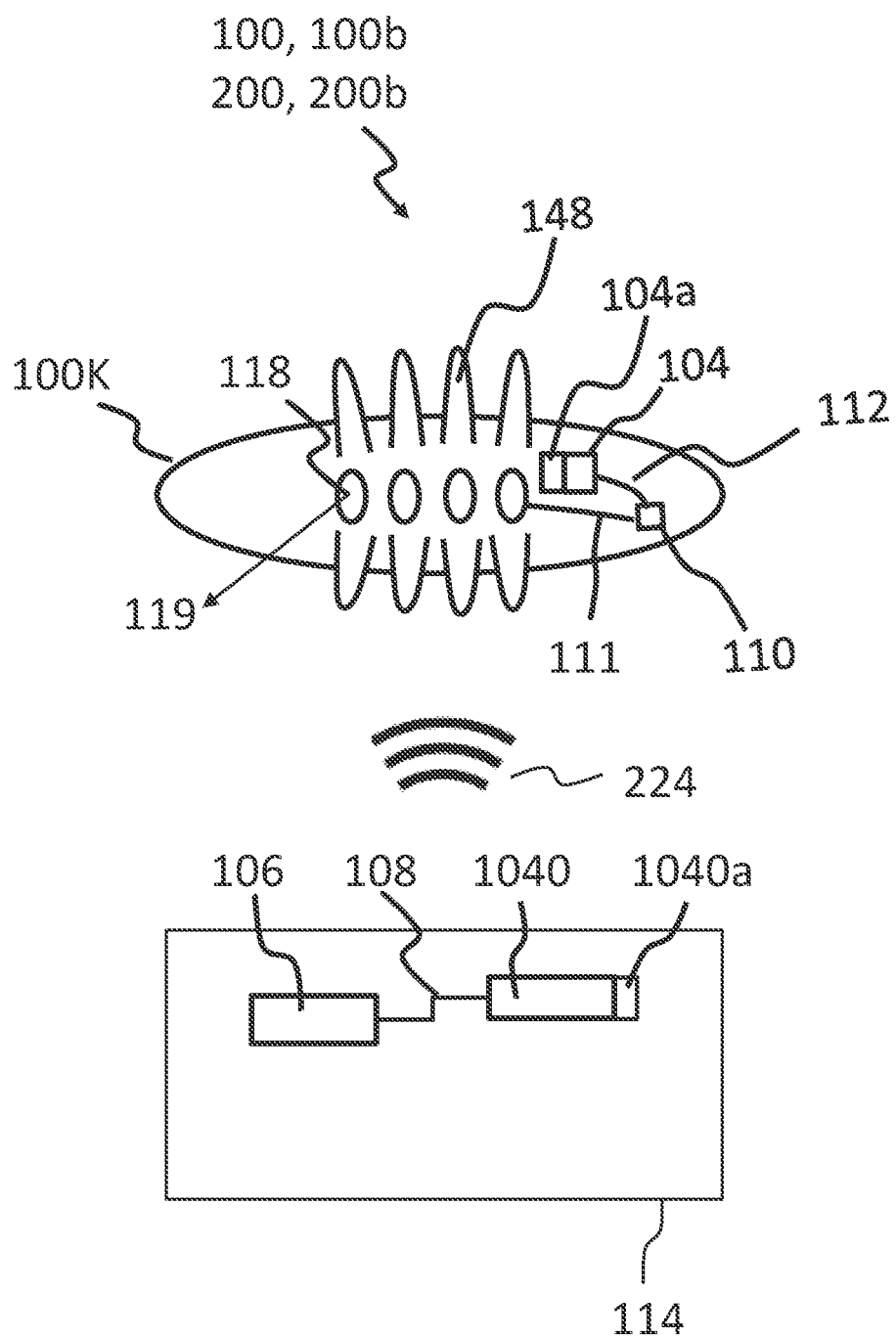
Figure 1C:
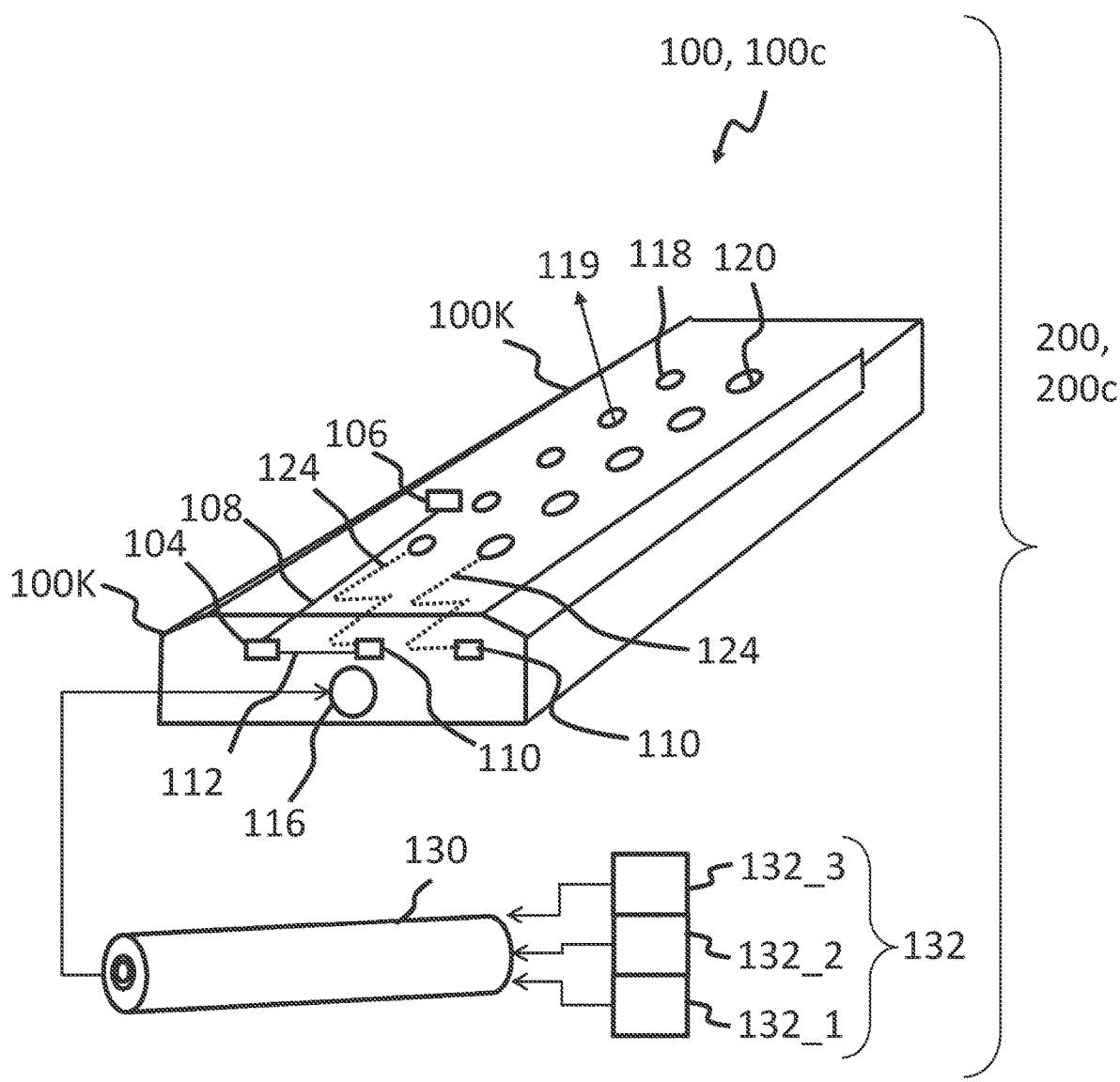

As shown in FIG. 1C, in various embodiments, the hair treatment agent in the treatment device 100 can be or can be accommodated in a cartridge 130. The cartridge 130 can be refillable, for example. The cartridge 130 can be introduced into the treatment device 100 in various embodiments, for example, by employing an opening 116.

The dosing valve can be part of the treatment device 100 in various embodiments. Alternatively, the dosing valve can be part of the cartridge 130.

In various embodiments, instead of using the cartridge 130, the hair treatment agent can be directly introduced into a receiving space of the treatment device 100.

In various embodiments, the system 200 for improving a hair condition can have a mixing device 132, by employing which the personalized hair treatment agent (as described above) can be preparable. In various embodiments, the personalized hair treatment agent can be prepared by employing a mixing device not belonging to the system 200 for improving a hair condition and provided in the cartridge, for example, in a beauty parlor, by another manufacturer, for example, an Internet retailer, or the like.

In the system 200a for improving a hair condition of FIG. 1A, in various embodiments, the sensor device, in this case the at least one sensor 106, can be integrated into the treatment device 100, 100a embodied as a hair band by way of example. The treatment device 100a can be configured, in various embodiments, to determine at least one hair treatment parameter and to control the hair treatment by employing the at least one actuator 110 by employing the integrated electronic circuit device 104 based on the hair condition parameter detected by employing the integrated sensor 106, wherein the hair treatment has an applying of the hair treatment agent and a mechanical and/or thermal treatment (for example, massaging the scalp and/or heating or cooling the hair 220H or the scalp).

The system 200b for improving a hair condition of FIG. 1B can, in various embodiments, correspond to the system 200a for improving a hair condition of FIG. 1A, but have a device body 100K designed brush-like which can be intended to be guided along the head during a treatment. A fixing in a position can also be possible in various embodiments. In contrast to the system 200a of FIG. 1A, in various embodiments, the sensor device 114 can be a device separate from the treatment device 100b, for example, as described above.

In the system 200c for improving a hair condition of FIG. 1C, in various embodiments, the device body 100K can be designed block-shaped, and further, the treatment device 100c can be provided with a dosing device 100c as described above. Furthermore, a mixing device 132 as described above can be part of the treatment system 200c.

Figure 1D:
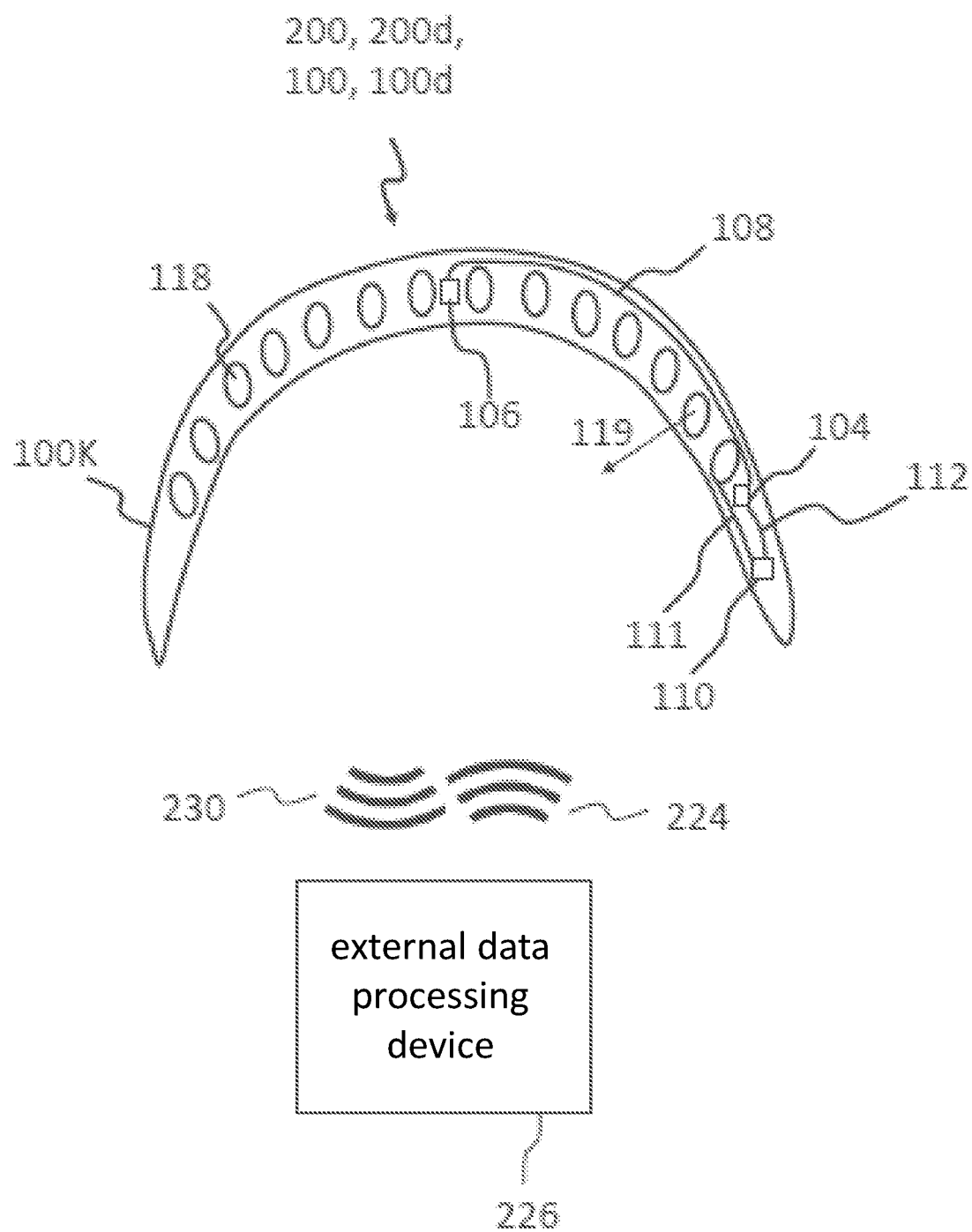

The system 200d for improving a hair condition of FIG. 1D can, in various embodiments, differ from the system 200a for improving a hair condition of FIG. 1A, to the extent that the treatment device 100c has a data exchange device 104a that can be configured to wirelessly transmit and receive data (illustrated as signals 224 and 230).

The system 200 for improving a hair condition, 200d can, in various embodiments, be configured to exchange data with an external data processing device 226 by employing the data exchange device 104a. The external data processing device can be, for example, an external computer, for example, a cloud.

As described above, the external data processing device 226 can be configured to receive the detected sensor data from the system 200d for improving a hair condition, to determine the control parameters and/or the at least one recommendation, and to transmit these back to the system 200c for improving a hair condition. That is, the system 200d for improving a hair condition can be configured, as described above, to indirectly determine the control or regulation parameters and/or the at least one recommendation.

Figure 1E:
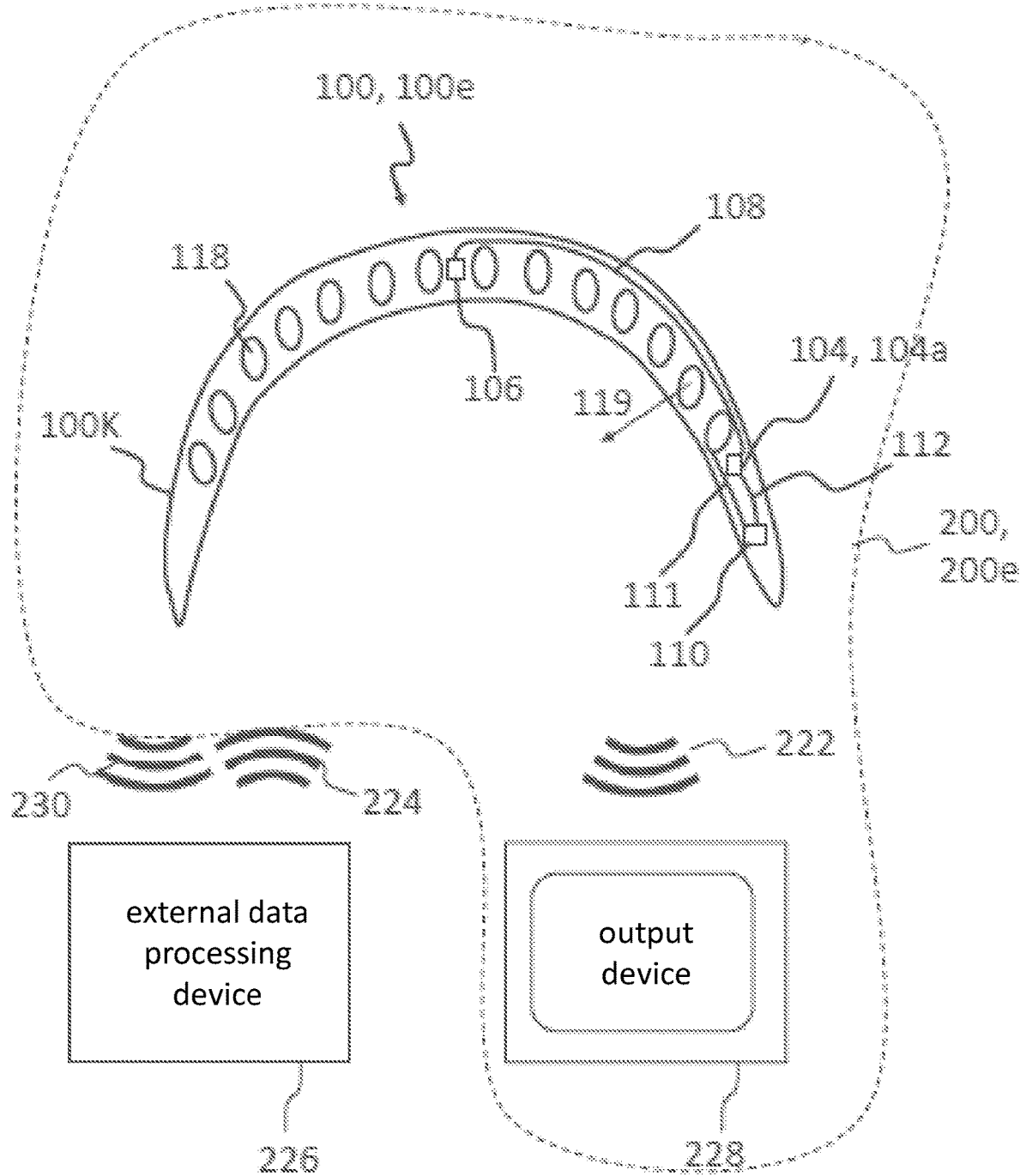

The system 200e for improving a hair condition, 200e of FIG. 1E, in various embodiments, can substantially correspond to the system 200d for improving a hair condition of FIG. 1D, but can be supplemented by an output device 228. By way of example, a screen, that is, a display device, is illustrated as an output device 228. Alternatively or additionally, however, the system 200e for improving a hair condition can have any type of output device 228, for example, as described above.

The output device 228, in various embodiments, can be configured to receive and output, for example, display, data (as a (for example, wireless) signal 222) from the treatment device 100d, for example, a recommendation determined by employing the electronic circuit device 104 and/or the external data processing device 226, for example, a hair treatment recommendation and/or a recommended hair growth and/or hair care agent or the like.

The system 200f for improving a hair condition of FIG. 1F, in various embodiments, can have a treatment device 100, 100e, which can be shaped like a helmet as described above and can have the illumination device 118, the sensor 106, and the electronic circuit device 104.

The system 200f can have a separate output device 228 which, as described above, can receive and output, for example, display, data from the treatment device 100f.

The treatment device 100e can, in various embodiments, be configured to wirelessly transmit and receive data 224, 230.

The system 200f for improving a hair condition can have a display device 228 in various embodiments.

The display device 228, in various embodiments, can be configured to receive and output data (as a signal 222) from the treatment device 100e, for example, as described above in FIG. 1E.

Figure 1G:
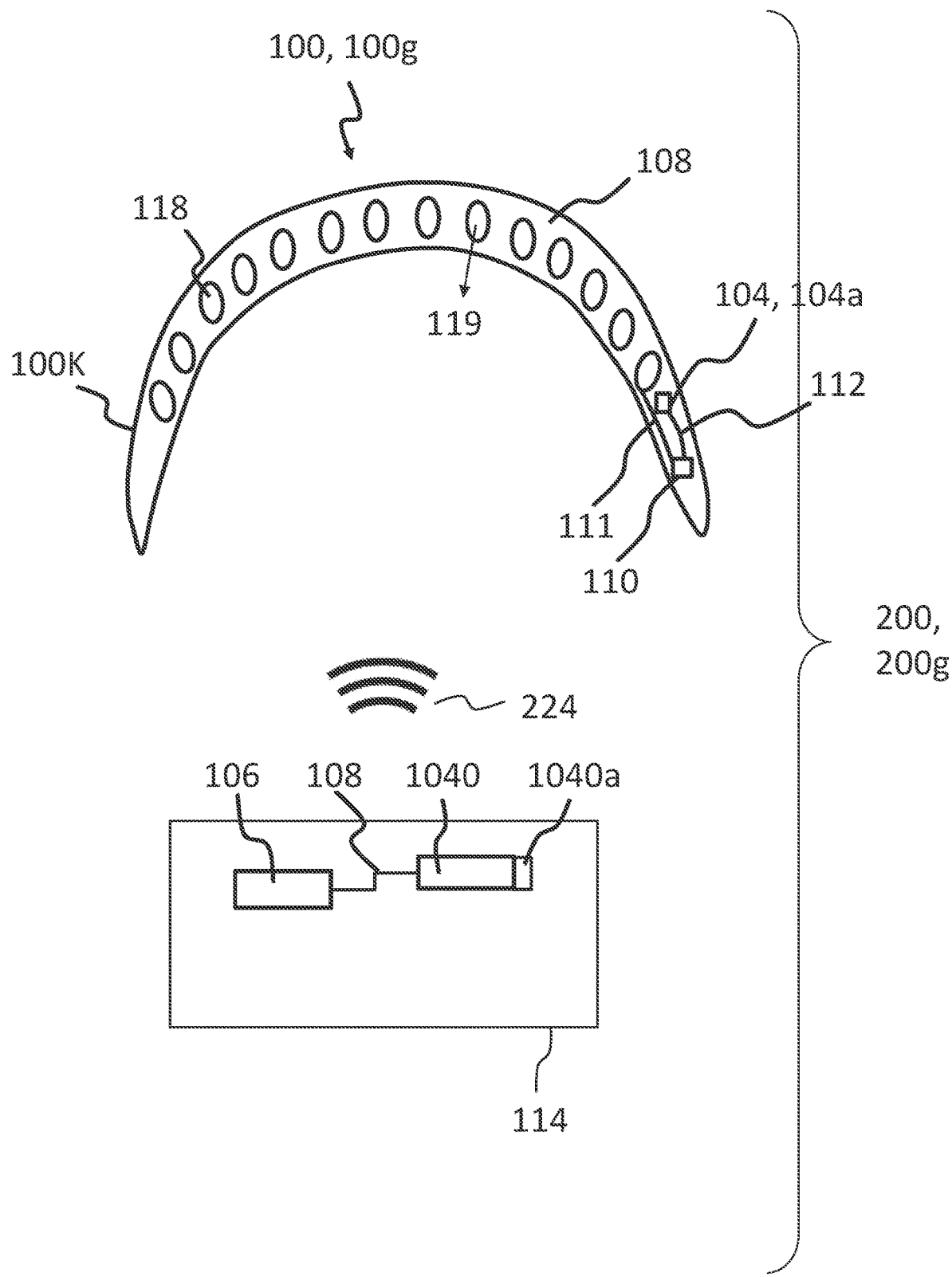

The system 200g for improving a hair condition of FIG. 1G can correspond substantially to the system 200b of FIG. 1B, except that the device body 100K is designed as a hair band and thus can be arranged in the hair 220H substantially in one position, instead of being used during a combing operation to treat the scalp or hair.

Figure 1H:
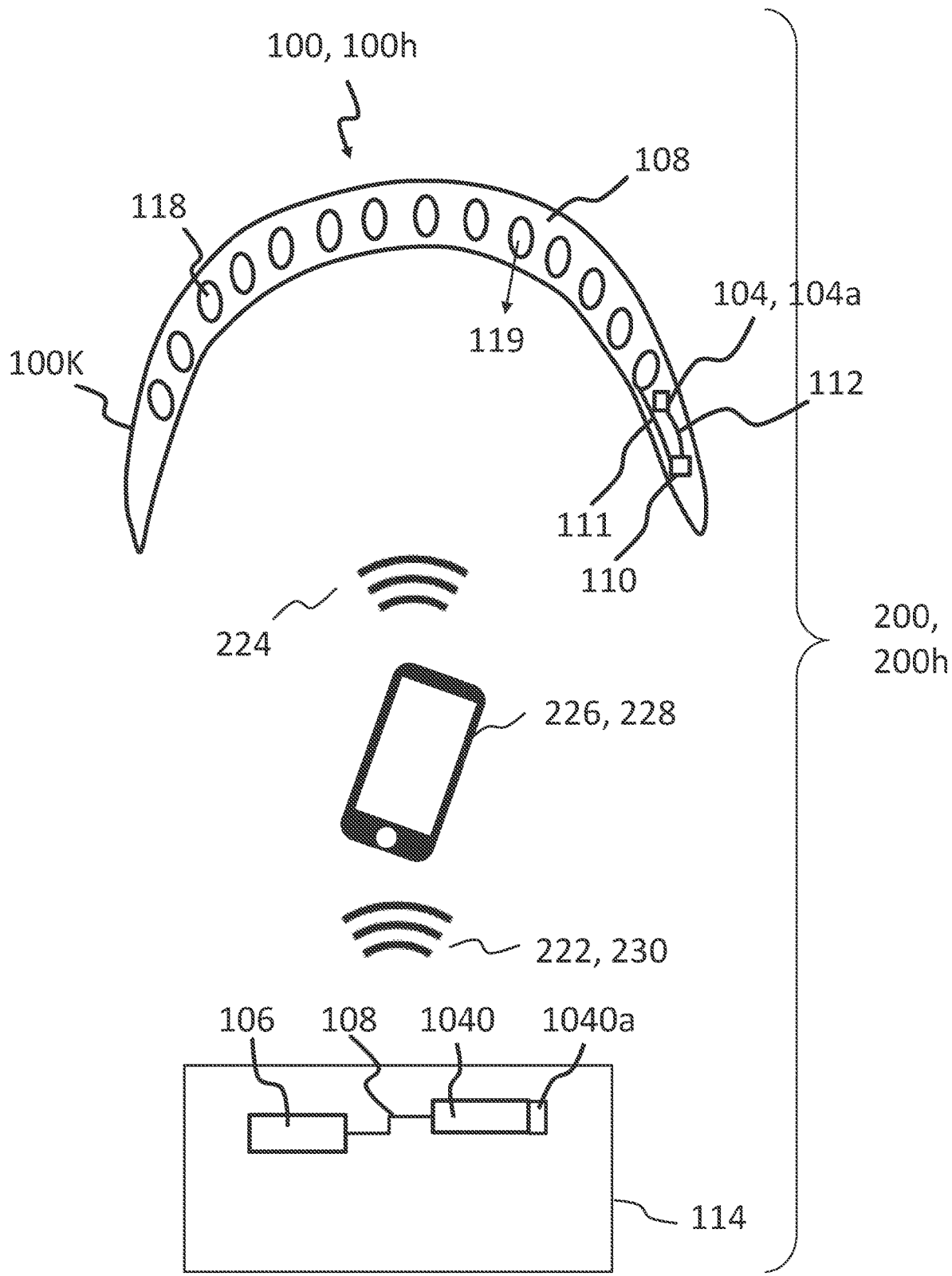

The system 200h for improving a hair condition of FIG. 1H, in various embodiments, can have a treatment device 100, 100h, which can be similar or identical in essential parts to the treatment device 100g of FIG. 1G.

In contrast to the system 200g for improving a hair condition of 1G, the treatment device 100h and the external sensor device 114 can be configured not to exchange their data directly with each other, but rather by employing a combined data processing and display device 226, 228 (for example, a smartphone, a tablet, a laptop, or the like). Expressed otherwise, the combined data processing and display device 226, 228 can act as the heart of the system 200g for improving a hair condition. For example, an app or a program can be installed on the combined data processing and display device 226, 228, which app or program can be configured to manage the detection of the sensor data and the control/regulation of the hair treatment parameters, where appropriate, for example, alternatively or in addition to the electronic circuit device 104 and/or the electronic circuit device 1040, to determine the control or regulation parameters and/or the recommendation and/or, where appropriate, alternatively or in addition to the treatment device 100h, to provide the recommendation, by employing the output device 228, for example, as a display, or acoustically, for example, by employing a speaker.

In various embodiments, the combined data processing and display device 226, 228 can further be configured to provide the sensor data to a (further) external data processing device 226, for example, a cloud, and to transmit from the (further) external data processing device 226 the control or regulation parameters and/or the recommendation of the treatment device 100f received therefrom and/or to provide the recommendation.

In various embodiments, to determine a hair condition, for example, a degree of hair damage or the like, a database can be used, as described above, in which the sensor data or, where appropriate, combinations of sensor data, the hair conditions (for example, degrees of hair damage) can be assigned. The database may have been previously created by employing experiments and stored, for example, in the data processing and display device 226, 228 and/or in at least one of the electronic circuit devices 104, 1040, and/or can be continually created, for example, using a cloud, using user data or supplemented and provided to the system 200g for improving a hair condition.

In various embodiments, the database can further provide a treatment and/or product recommendation based on the hair condition, for example, degree of hair damage. When determining the treatment and/or product recommendation, a further information item provided by the user 220 can also be included, for example, as described above.

The detected (measured) sensor values can, as described above, either be evaluated directly in the hair treatment device 100, for example, by employing the electronic circuit device 104, or indirectly evaluated by being transmitted to an external data processing device 226 to be evaluated there, for example, as described above. In this case, the sensor data or parts of the sensor data can be evaluated in various embodiments by employing a comparison with (for example, empirically obtained) database entries.

In various embodiments, the determined hair treatment agent, for example, hair growth agent or hair care agent, can be applied to the hair by employing the treatment device or the system for improving a hair condition, wherein control or regulation parameters for dosing the hair treatment agent by employing the electronic circuit device 104, the electronic circuit device 1040 and/or the external data processing device 226 and/or the further external data processing device can be provided.

The system 200j for improving a hair condition FIG. 1J, in various embodiments, can have a treatment device 100, 100j, which can be similar or identical in essential parts to the treatment device 100h of FIG. 1H.

The separate sensor device 114 can, as already described in connection with FIG. 1G, have a smartphone, a tablet, a laptop or the like, for example, the camera and/or a microphone of the smartphone/tablet/laptop 114 can be used as a sensor 106 or part of the sensor. However, thanks to a touch-sensitive screen or a combination of keyboard and screen and/or mouse and screen, the sensor device 114 of the system 200j for improving a hair condition can simultaneously be used as an input and/or output device 228, and a processor of the smartphone/tablet/laptop can be used as the electronic circuit device 1040 of the sensor device 114 or as the data processing device 226, for example, by employing a software (for example, app) installed there, and provide functions as described above for the electronic circuit device 1040 of the sensor device 114 or as the data processing device 226.

Furthermore, the hair band in various embodiments can be designed in several parts (here formed in two parts by way of example), so that one part is or can be arranged stationary, and a further part can be pivotably movable along the head. It can be thus possible to make accessible positions for the hair treatment remote from the hair band (part) fixed in a position by employing the device.

FIG. 2A shows a schematic representation of an application of a system for improving a hair condition according to various embodiments, and FIG. 2B shows a schematic representation of an application of a system 200h for improving a hair condition according to various embodiments.

As shown in FIG. 2A, the treatment device 100a can be used in a usual way for the treatment device for hair treatment. A hair band is illustrated.

In contrast to the conventional system for improving a hair condition, system 200 for improving a hair condition according to various embodiments can be configured, during the hair treatment, for example, as described above, to detect at least one sensor value by employing a sensor 106 and to control or regulate at least one hair treatment parameter, wherein the hair treatment has at least the illumination of the scalp with light, as described above.

As shown in FIG. 2B, the system 200h for improving a hair condition can be used for a hair treatment. As described above, an external sensor device 114 can be used to determine at least one hair condition parameter, for example, a hair density, a degree of hair damage or the like. For this purpose, the external sensor device 114 can be brought into optical and/or physical contact with the hair 220H of the user 220.

As described above, the at least one sensor value and/or a hair condition parameter determined therefrom and/or a control or regulation parameter can be transmitted to the combined data processing/display device 226, 228 (shown as signal 222, 230) and the at least one sensor value and/or or a hair condition parameter determined therefrom and/or a control or regulation parameter can be transmitted to the treatment device 100g, for example, for controlling and/or regulating the at least one actuator 110 and/or for displaying the at least one recommendation.

Shown here is a transmission of the at least one sensor value and/or a hair condition parameter determined therefrom and/or a control or regulation parameter to the treatment device 100h before using the treatment device 100h. In various embodiments, the transmission can also be made simultaneously with the use.

In various embodiments, the other hair treatment devices and system for improving a hair condition described above can be used analogously similarly as described here by way of example for two systems for improving a hair condition.

FIG. 3 shows a flowchart 300 of a method for the cosmetic treatment of hair of a user according to various embodiments.

In various embodiments, the method for cosmetically treating hair of a user can have a detecting of at least one hair condition parameter prior to a treatment or during a treatment by employing a system according to various embodiments, by employing the at least one sensor by employing a system for improving a hair condition according to various embodiments (in 310) and an illumination of a scalp of the user by employing the illumination device based on the received detected hair condition parameter and/or the treatment parameter determined therefrom (in 320).

Programming, for example, software, can be used in various embodiments for the determinations described above. In this case, any software that provides a functionality described above can be used. In various embodiments, for example, in a case that a smartphone, a tablet or the like is used to carry out the method for the cosmetic treatment of hair of a user according to various embodiments, the software can be provided as an app.

In various embodiments, the circuit device integrated into the treatment device and/or an external data processing device, for example, a smartphone, a tablet, a laptop, a smart mirror, an iPad, or the like can be suitable in order to be used for an execution of the method for providing a hair condition information item and/or an environmental condition information item, for example, in determination operations, for example, by comparison with a database/reference values or the like. In various embodiments, the programming/software does not need to be provided on the smartphone, tablet, laptop, etc. For example, it can be sufficient when the circuit device integrated into the treatment device and/or the smartphone or the like is connected through the Internet, by employing WLAN or in another common way to a (for example, a further) external data processing device, for example, a computer, for example, a cloud. In such a case, the calculations can be executed, for example, by employing the (further) external data processing device, for example, by employing the computer, and the result can be provided to the smartphone/tablet or the like and/or the internal circuit device, wherein the treatment device can be configured to use the control commands determined by employing the external data processing device to control or regulate the at least one hair treatment parameter, for example, to control or regulate a corresponding actuator.

Further advantageous embodiments of the method are apparent from the description of the device and vice versa.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A system for improving a hair condition, having:
   a sensor device having at least one sensor for detecting a hair condition parameter wherein the hair condition parameter is a cysteic acid content; and
   a treatment device having:
   an illumination device for illuminating a scalp of a user with light;
   a hair treatment device including at least one of an applicator of a cosmetic treatment agent, a massage device, a heating device and a cooling device, and
   an electronic circuit device which is coupled to the sensor device for determining a hair treatment parameter in response to the detected hair condition parameter wherein the hair treatment parameter includes a hair treatment agent and a light wavelength, the electronic circuit device further configured control the hair treatment device to perform at least one of apply the cosmetic treatment agent, perform a massage, heat the scalp and the hair, and to cool the scalp and the hair in response to at least one of the detected hair condition parameter and the treatment parameter; and
   the electronic circuit device being configured to control an illumination of the scalp of the user with light having the light wavelength by employing the illumination device based on the hair treatment parameter, the electronic circuit device being further configured to control a dosing device for the hair treatment agent based on the hair treatment parameter.

2. The system according to claim 1,
wherein the treatment device has a hair band, a hair clip or a helmet.

3. The system according to claim 1,
wherein the at least one sensor has at least one from a group of sensors, the group of sensors having:
a camera for recording an image by employing visible light, UV light and/or near-infrared light for determining a hair density, a degree of hair damage, a curl, a hair color and/or a hair thickness;
a microscope for determining a degree of hair damage and/or a hair thickness;
a spectrometer for recording a spectrum of visible light, UV light and/or near-infrared light to determine a degree of hair damage and/or a hair moisture content; and
an acoustic sensor for determining a degree of hair damage.

4. The system according to claim 1,
wherein the sensor device and the treatment device are separate devices.

5. The system according to claim 1,
wherein at least a part of the sensor device and the treatment device form an integrated unit.

6. The system according to claim 1,
wherein the electronic circuit device has a wireless data exchange device.

7. The system of claim 1, further having:
an input device and/or an output device.

8. The system according to claim 1,
wherein the light for illuminating the scalp of the user has a wavelength of about 640 to about 780 nm.

9. A method for improving a cosmetic hair condition of a user, having:
before treatment or during treatment by employing a system according to claim 1, illuminating a scalp of the user by employing the illumination device based on the received detected hair condition parameter and/or the treatment parameter determined therefrom.

10. The method according to claim 9, further having:
treating the hair by employing the at least one further treatment element based on the received detected hair condition parameter and/or the treatment parameter determined therefrom.

11. The method according to claim 10,
wherein the treatment by employing the at least one further treatment element has an applying of a cosmetic treatment agent to the hair or scalp, a massaging of the scalp, a heating the scalp and/or hair and/or a cooling of the scalp and/or the hair.

12. The method according to claim 11, wherein the cosmetic treatment agent is automatically reordered based on a fill level amount.

13. The method according to claim 11,
wherein the cosmetic treatment agent is automatically reordered based on a fill level amount.

14. The method according to claim 10,
wherein the determining of the at least one treatment parameter is carried out from the at least one hair condition parameter in the electronic circuit device.

15. The method according to claim 10,
wherein the detection of the hair condition and the illumination of the scalp are executed repeatedly, wherein the detection of the hair condition is executed at a substantially same location of the hair and/or the scalp with each repeated execution.

16. The method according to claim 9,
wherein the detection of the hair condition and the illumination of the scalp are executed repeatedly, wherein the detection of the hair condition is executed at a substantially same location of the hair and/or the scalp with each repeated execution.

* * * * *